US012601699B2

(12) United States Patent
Zambon et al.

(10) Patent No.: US 12,601,699 B2
(45) Date of Patent: Apr. 14, 2026

(54) FLUID CONDITION SENSING SYSTEM AND METHODS

(71) Applicant: Donaldson Company, Inc., Bloomington, MN (US)

(72) Inventors: Nathan D. Zambon, Cedar Falls, IA (US); Danny W. Miller, Ackley, IA (US); Chad M. Goltzman, Bloomington, MN (US); Giancarlo M. Izzi, Minneapolis, MN (US); Davis B. Moravec, Burnsville, MN (US); Michael J. Cronin, Apple Valley, MN (US)

(73) Assignee: Donaldson Company, Inc., Bloomington, MN (US)

( * ) Notice: Subject to any disclaimer, the term of this patent is extended or adjusted under 35 U.S.C. 154(b) by 254 days.

(21) Appl. No.: 17/851,433

(22) Filed: Jun. 28, 2022

(65) Prior Publication Data

US 2022/0412912 A1     Dec. 29, 2022

Related U.S. Application Data

(60) Provisional application No. 63/216,153, filed on Jun. 29, 2021.

(51) Int. Cl.
G01N 27/22      (2006.01)
G01D 21/02      (2006.01)
(Continued)

(52) U.S. Cl.
CPC ........... G01N 27/221 (2013.01); G01D 21/02 (2013.01); G01N 27/046 (2013.01); G01N 27/223 (2013.01); G01N 33/2888 (2013.01)

(58) Field of Classification Search
CPC .. G01N 27/221; G01N 27/046; G01N 27/223; G01N 33/2888; G01D 21/02;
(Continued)

(56) References Cited

U.S. PATENT DOCUMENTS 4,733,556 A     3/1988  Meitzler et al.
5,540,086 A     7/1996  Park et al.
(Continued)

FOREIGN PATENT DOCUMENTS

AU       2008237666      6/2012
CA         2156686       2/1997
(Continued)

OTHER PUBLICATIONS

"FPS2800B12C4 Fluid Property Sensor," TE Connectivity Sensor Solutions Product Specification Sheet, Sep. 2015 (5 pages).
(Continued)

*Primary Examiner* — Alvaro E Fortich
(74) *Attorney, Agent, or Firm* — Pauly, DeVries Smith & Deffner LLC

(57) ABSTRACT

Embodiments herein relate to oil condition sensing systems and related methods. In a first aspect, an oil condition sensing system is included having a control circuit, a temperature sensor, and a fluid property sensor, wherein the fluid property sensor measures fluid properties including at least dielectric constant and the oil condition sensing system is configured to automatically detect when an oil change event has occurred, record the fluid property sensor data as new baseline fluid property data after an oil change event has occurred, and evaluate the condition of an engine oil based on a comparison with the baseline fluid property data. The oil condition sensing system can be configured to automatically detect the oil change event by evaluating signals from the fluid property sensor and interpret a change in dielectric
(Continued)

constant and/or viscosity crossing a threshold value as an oil change event. Other embodiments are also included herein.

20 Claims, 12 Drawing Sheets

(51) Int. Cl.
   G01N 27/04 (2006.01)
   G01N 33/28 (2006.01)

(58) Field of Classification Search
   CPC ....... F01M 2011/14; F01M 2011/1413; F01M 2011/146; F01M 2011/1473; F01M 2011/148; F01M 11/10; F16N 2200/00; F16N 2200/10; F16N 2200/12; F16N 2210/04; F16N 2230/00; F16N 2230/02; F16N 2260/18
   See application file for complete search history.

(56) References Cited

U.S. PATENT DOCUMENTS

| | | | |
|---|---|---|---|
| 5,604,441 | A | 2/1997 | Freese et al. |
| 6,268,737 | B1 | 7/2001 | Marszalek |
| 6,553,812 | B2 | 4/2003 | Park et al. |
| 6,750,763 | B2 | 6/2004 | Ismail et al. |
| 6,776,024 | B2 | 8/2004 | Jakoby |
| 6,867,603 | B2 | 3/2005 | Nicholson et al. |
| 6,957,565 | B2 | 10/2005 | Matsiev et al. |
| 7,043,969 | B2 | 5/2006 | Matsiev et al. |
| 7,204,128 | B1 | 4/2007 | Liu et al. |
| 7,370,514 | B2 | 5/2008 | Halalay et al. |
| 7,677,086 | B2 | 3/2010 | Albertson et al. |
| 7,835,875 | B2 | 11/2010 | Halalay et al. |
| 7,908,051 | B2 | 3/2011 | Oesterling |
| 7,908,912 | B2 | 3/2011 | Van et al. |
| 8,115,501 | B2 | 2/2012 | Albertson et al. |
| 8,127,597 | B2 | 3/2012 | Staley et al. |
| 8,746,408 | B2 | 6/2014 | Albertson et al. |
| 9,175,595 | B2 | 11/2015 | Ceynow et al. |
| 9,176,086 | B2 | 11/2015 | Qi |
| 9,267,872 | B2 | 2/2016 | Haeusler et al. |
| 9,714,931 | B2 | 7/2017 | Prabhu et al. |
| 11,261,766 | B1 * | 3/2022 | Dudar .................... F02D 41/22 |
| 2003/0005751 | A1 | 1/2003 | Berndorfer et al. |
| 2005/0039521 | A1 * | 2/2005 | Han ....................... F01M 11/10 701/29.5 |
| 2005/0209796 | A1 * | 9/2005 | Kolosov ............... G01N 11/16 702/52 |
| 2009/0063060 | A1 * | 3/2009 | Sun ...................... G01F 23/268 702/52 |
| 2010/0307230 | A1 | 12/2010 | Gilch et al. |
| 2012/0316752 | A1 | 12/2012 | Krishevsky |
| 2015/0075268 | A1 * | 3/2015 | Qi .......................... G01N 27/02 73/114.55 |
| 2015/0082871 | A1 * | 3/2015 | Zha .................... G01N 33/2888 73/53.05 |
| 2017/0102308 | A1 * | 4/2017 | Gillette, II ............. G01N 11/00 |
| 2018/0231518 | A1 | 8/2018 | Vaidya et al. |
| 2019/0232971 | A1 * | 8/2019 | Vijayakumar ...... B60W 50/045 |
| 2019/0346389 | A1 | 11/2019 | Gayrard et al. |
| 2020/0378283 | A1 * | 12/2020 | Zhang ................ G01N 33/2888 |

FOREIGN PATENT DOCUMENTS

| | | |
|---|---|---|
| DE | 10345253 | 5/2005 |
| EP | 2096434 | 8/2013 |
| JP | 3804976 | 5/2006 |
| WO | 03054482 | 7/2003 |
| WO | 2020012058 | 1/2020 |
| WO | 2023278434 | 1/2023 |

OTHER PUBLICATIONS

"Oil and Fuel Monitoring Using the ViSmart Voscosity Sensor," SenGenuity Article published Jun. 1, 2013 and available at URL <web.archive.org/web/20130601034522/http://machinerylubrication.com/Articles/Print/2071> (8 pages).
"Oil Quality Sensor 2," Des-Case Oil quality sensor technical specifications sheet available at least as early as 2021 at URL <https://www.rmfsystems.com/products/condition-monitoring/sensors/oil-quality-sensor/> (4 pages).
"Trident Online Oil Quality Sensors," Poseidon Systems Inline Oil Quality Sensors available at least as early as Aug. 6, 2020 at URL <https://www.poseidonsys.com/products-and-services/products/inline-oil-quality-sensors/> (6 pages).
Clark, Ryan James "On-Board Monitoring of Engine Oil," Master's Thesis Western Michigan University 2011 (124 pages).
Fecek, David P. "Online Detection of Water and Coolant in Engine Oil," Master's Thesis for the Pennsylvania State University 2017 (125 pages).
Gayrard, Fabien, et al. "Engine Oil Condition Monitoring with FPS2800 Oil Property Sensor," TE Connectivity White Paper Document published May 2020. (24 pages).
"International Search Report and Written Opinion," for PCT Application No. PCT/US2022/035302 mailed Oct. 31, 2022 (12 pages).
"International Preliminary Report on Patentability," for PCT Application No. PCT/US2022/035302 mailed Jan. 11, 2024.
"Communication pursuant to Article 94(3) EPC," for European Patent Application No. 22748524.0 mailed Nov. 11, 2024 (5 pages).

* cited by examiner

| | VISCOSITY | DENSITY | DIELECTRIC CONSTANT | RESISTIVITY |
|---|---|---|---|---|
| FUEL | ↓↓↓ | ↑ or ↓ | ↑ or ↓ | ↑ or ↓ |
| SOOT | ↑↑ | ↑ | ↑↑↑ | ↓ |
| METAL | ↑ | ↑ | ↑ | NC |
| WATER | NC | NC | ↑↑ | ↓↓ |
| COOLANT | NC | NC | ↑ | ↓ |
| TBN/TAN | NC | NC | NC | ↑↑↑ or ↓↓↓ |

| | | | | | |
|---|---|---|---|---|---|
| ↑↑↑ | Large Increase | ↓↓↓ | Large Decrease | NC | No Change |
| ↑↑ | Medium Increase | ↓↓ | Medium Decrease | | |
| ↑ | Small Increase | ↓ | Small Decrease | | |

FLUID CONDITION SENSING SYSTEM AND METHODS

This application claims the benefit of U.S. Provisional Application No. 63/216,153, filed Jun. 29, 2021, the content of which is herein incorporated by reference in its entirety.

FIELD

Embodiments herein relate to fluid condition sensing systems and related methods.

BACKGROUND

Engine lubrication systems serve an important role in the operation of various types of engines including providing for lubrication, cooling, cleaning and the like. However, engine oil tends to breakdown over time losing effectiveness. In addition, engine oil can become contaminated with various other components over time including, but not limited to, water, fuel, coolant, soot, metal, acids/bases, and the like.

Beyond engine oils, many other fluids are used for lubrication, power transfer (such as in the case of hydraulic fluids), or other purposes and may also break down or otherwise become contaminated over time.

SUMMARY

Embodiments herein relate to fluid condition sensing systems and related methods. In a first aspect, a fluid condition sensing system is included having a control circuit, a temperature sensor in signal communication with the control circuit, and a fluid property sensor in signal communication with the control circuit. The fluid property sensor measures fluid properties including at least dielectric constant. The fluid condition sensing system can be configured to automatically detect when a fluid change event has occurred, record the fluid property sensor data as new baseline fluid property data after a fluid change event has occurred, and evaluate the condition of the fluid based on a comparison with the baseline fluid property data.

In a second aspect, in addition to one or more of the preceding or following aspects, or in the alternative to some aspects, the fluid condition sensing system can be configured to automatically detect the fluid change event by evaluating signals from the fluid property sensor and interpret a change in dielectric constant crossing a threshold value as an absolute value, an amount of change as an absolute value, a relative value, or an amount of change as a relative value, as a fluid change event.

In a third aspect, in addition to one or more of the preceding or following aspects, or in the alternative to some aspects, the fluid property sensor also measures viscosity of fluid.

In a fourth aspect, in addition to one or more of the preceding or following aspects, or in the alternative to some aspects, further can include a drain plug sensor, wherein the drain plug sensor can be in signal communication with the control circuit.

In a fifth aspect, in addition to one or more of the preceding or following aspects, or in the alternative to some aspects, the fluid condition sensing system can be configured to automatically detect a fluid change event by evaluating signals from the fluid property sensor and the drain plug sensor and interpret a change in dielectric constant crossing a threshold value that is correlated with a drain plug removal event as a fluid change event.

In a sixth aspect, in addition to one or more of the preceding or following aspects, or in the alternative to some aspects, the drain plug sensor can include a short-range wireless transceiver, wherein the short-range wireless transceiver can be configured to be mounted in a fixed relationship to a drain pan, and a short-range wireless antenna, wherein the short-range wireless antenna can be configured to be mounted on a drain plug.

In a seventh aspect, in addition to one or more of the preceding or following aspects, or in the alternative to some aspects, the fluid condition sensing system can be configured to issue an alert when a current dielectric constant value differs from a recorded dielectric constant value by an amount crossing a threshold value.

In an eighth aspect, in addition to one or more of the preceding or following aspects, or in the alternative to some aspects, the fluid condition sensing system can be configured to estimate a time when a fluid change can be needed based on a rate of change of measured dielectric constant values versus the baseline dielectric constant value.

In a ninth aspect, in addition to one or more of the preceding or following aspects, or in the alternative to some aspects, the new baseline fluid property data can be stored in memory in electronic communication with the control circuit.

In a tenth aspect, in addition to one or more of the preceding or following aspects, or in the alternative to some aspects, the new baseline fluid property data can be sent through a communication network for storage in the cloud.

In an eleventh aspect, in addition to one or more of the preceding or following aspects, or in the alternative to some aspects, the fluid condition sensing system can be configured to send an alert when new baseline fluid property data, after a fluid change event has occurred, differs from a predetermined expected value by a threshold amount.

In a twelfth aspect, in addition to one or more of the preceding or following aspects, or in the alternative to some aspects, the fluid condition sensing system can be configured to identify a type of fluid present after a detected fluid change event based on at least one type of data from the fluid property sensor selected from viscosity and dielectric constant value and send an alert indicating the type of fluid present.

In a thirteenth aspect, in addition to one or more of the preceding or following aspects, or in the alternative to some aspects, the fluid condition sensing system can be configured to identify a type of fluid present after a detected fluid change event based on at least one type of data from the fluid property sensor and send an alert to a fleet manager if the type of fluid can be out of specification.

In a fourteenth aspect, in addition to one or more of the preceding or following aspects, or in the alternative to some aspects, the fluid property sensor measures viscosity, density, impedance, dielectric constant, and resistivity of fluid.

In a fifteenth aspect, in addition to one or more of the preceding or following aspects, or in the alternative to some aspects, the fluid condition sensing system can be configured to determine a fluid contamination state based on data from the fluid property sensor.

In a sixteenth aspect, in addition to one or more of the preceding or following aspects, or in the alternative to some aspects, the fluid contamination state includes the presence and/or amount of at least one of ingressed contaminants and generated contaminants.

In a seventeenth aspect, in addition to one or more of the preceding or following aspects, or in the alternative to some aspects, the fluid contamination state includes at least one of oxidation state, water contamination, coolant contamination, fuel contamination, soot contamination, metal contamination, total base number value, total acid number value, and incorrect fluid presence.

In an eighteenth aspect, in addition to one or more of the preceding or following aspects, or in the alternative to some aspects, the fluid condition sensing system can be configured to determine fluid water contamination and coolant contamination when a measured temperature of the fluid is less than a boiling temperature of water at a location of the fluid being evaluated by the fluid condition sensing system.

In a nineteenth aspect, in addition to one or more of the preceding or following aspects, or in the alternative to some aspects, the fluid condition sensing system can be configured to determine fluid water contamination and coolant contamination when a measured temperature of the fluid is less than 100 degrees Celsius.

In a twentieth aspect, in addition to one or more of the preceding or following aspects, or in the alternative to some aspects, the fluid condition sensing system can be configured to determine fluid fuel contamination when a measured temperature of the fluid is less than 110 degrees Celsius.

In a twenty-first aspect, in addition to one or more of the preceding or following aspects, or in the alternative to some aspects, the fluid condition sensing system can be configured to determine fluid oxidation and soot contamination when a measured temperature of the fluid can be from 90 to 125 degrees Celsius.

In a twenty-second aspect, in addition to one or more of the preceding or following aspects, or in the alternative to some aspects, the fluid condition sensing system can be configured to classify the fluid contamination state as having a slow evolution speed or a high evolution speed.

In a twenty-third aspect, in addition to one or more of the preceding or following aspects, or in the alternative to some aspects, the fluid condition sensing system can be configured to classify the fluid contamination state using current data reflecting viscosity, density, dielectric constant, and resistivity in comparison with baseline data for the same.

In a twenty-fourth aspect, in addition to one or more of the preceding or following aspects, or in the alternative to some aspects, the fluid condition sensing system can be configured to classify the fluid contamination state as being coolant or water contamination if dielectric constant increases, viscosity can be stable, and resistivity decreases.

In a twenty-fifth aspect, in addition to one or more of the preceding or following aspects, or in the alternative to some aspects, the fluid condition sensing system can be configured to classify the fluid contamination state as being fuel dilution if viscosity increases and other parameters can be stable.

In a twenty-sixth aspect, in addition to one or more of the preceding or following aspects, or in the alternative to some aspects, the fluid condition sensing system can be configured to classify the fluid contamination state as being soot contamination if viscosity increases and dielectric constant increases.

In a twenty-seventh aspect, in addition to one or more of the preceding or following aspects, or in the alternative to some aspects, the fluid condition sensing system can be configured to evaluate geolocation data when automatically detecting when the fluid change event has occurred.

In a twenty-eighth aspect, in addition to one or more of the preceding or following aspects, or in the alternative to some aspects, the fluid condition sensing system can be configured to normalize dielectric constant data based on temperature data.

In a twenty-ninth aspect, in addition to one or more of the preceding or following aspects, or in the alternative to some aspects, the fluid can include a hydrocarbon fluid.

In a thirtieth aspect, in addition to one or more of the preceding or following aspects, or in the alternative to some aspects, the fluid can include a lubricating oil.

In a thirty-first aspect, in addition to one or more of the preceding or following aspects, or in the alternative to some aspects, the fluid can include a hydraulic fluid.

In a thirty-second aspect, in addition to one or more of the preceding or following aspects, or in the alternative to some aspects, the fluid can include at least one selected from the group consisting of an engine oil, a transmission fluid, a compressor oil or fluid, and a pump oil or fluid.

In a thirty-third aspect, a fluid condition sensing system can be included having a control circuit, a temperature sensor in signal communication with the control circuit, and a fluid property sensor in signal communication with the control circuit, wherein the fluid property sensor measures fluid properties including at least fluid acid number. The fluid condition sensing system can be configured to automatically detect when a fluid change event has occurred, record the fluid property sensor data as new baseline fluid property data after a fluid change event has occurred, and evaluate the condition of the fluid based on a comparison with the baseline fluid property data.

In a thirty-fourth aspect, in addition to one or more of the preceding or following aspects, or in the alternative to some aspects, the fluid condition sensing system can be configured to automatically detect the fluid change event by evaluating signals from the fluid property sensor and interpret a change in viscosity crossing a threshold value as an absolute value, an amount of change as an absolute value, a relative value, or an amount of change as a relative value, as a fluid change event.

In a thirty-fifth aspect, in addition to one or more of the preceding or following aspects, or in the alternative to some aspects, the fluid condition sensing system can be configured to normalize viscosity data based on temperature data.

In a thirty-sixth aspect, in addition to one or more of the preceding or following aspects, or in the alternative to some aspects, the fluid property sensor measures dielectric constant of engine fluid.

In a thirty-seventh aspect, in addition to one or more of the preceding or following aspects, or in the alternative to some aspects, further can include a drain plug sensor, wherein the drain plug sensor can be in signal communication with the control circuit.

In a thirty-eighth aspect, in addition to one or more of the preceding or following aspects, or in the alternative to some aspects, the fluid condition sensing system can be configured to automatically detect a fluid change event by evaluating signals from the fluid property sensor and the drain plug sensor and interpret a change in viscosity crossing a threshold value that is correlated with a drain plug removal event as a fluid change event.

In a thirty-ninth aspect, in addition to one or more of the preceding or following aspects, or in the alternative to some aspects, the drain plug sensor can include a short-range wireless transceiver, wherein the short-range wireless transceiver can be configured to be mounted in a fixed relationship to a drain pan, and a short-range wireless antenna, wherein the short-range wireless antenna can be configured to be mounted on a drain plug.

In a fortieth aspect, in addition to one or more of the preceding or following aspects, or in the alternative to some aspects, the fluid condition sensing system can be configured to utilize viscosity sensor data only when a measured temperature falls within a predetermined temperature range.

In a forty-first aspect, in addition to one or more of the preceding or following aspects, or in the alternative to some aspects, the predetermined temperature range can include from 30 to 140 degrees Celsius.

In a forty-second aspect, in addition to one or more of the preceding or following aspects, or in the alternative to some aspects, the predetermined temperature range can include from 90 to 125 degrees Celsius.

In a forty-third aspect, in addition to one or more of the preceding or following aspects, or in the alternative to some aspects, the fluid condition sensing system can be configured to issue an alert when a current viscosity value differs from a recorded viscosity value by an amount crossing a threshold value.

In a forty-fourth aspect, in addition to one or more of the preceding or following aspects, or in the alternative to some aspects, the fluid condition sensing system can be configured to estimate a time when a fluid change is needed based on a rate of change of measured viscosity values versus the baseline viscosity value.

In a forty-fifth aspect, in addition to one or more of the preceding or following aspects, or in the alternative to some aspects, the new baseline fluid property data can be stored in memory in electronic communication with the control circuit.

In a forty-sixth aspect, in addition to one or more of the preceding or following aspects, or in the alternative to some aspects, the new baseline fluid property data can be sent through a communication network for storage in the cloud.

In a forty-seventh aspect, in addition to one or more of the preceding or following aspects, or in the alternative to some aspects, the fluid condition sensing system can be configured to send an alert when new baseline fluid property data after a fluid change event has occurred differs from a predetermined expected value by a threshold amount.

In a forty-eighth aspect, in addition to one or more of the preceding or following aspects, or in the alternative to some aspects, the fluid condition sensing system can be configured to identify a type of fluid present after a detected fluid change event based on at least one type of data from the fluid property sensor selected from viscosity and dielectric properties and send an alert indicating the type of fluid present.

In a forty-ninth aspect, in addition to one or more of the preceding or following aspects, or in the alternative to some aspects, the fluid condition sensing system can be configured to identify a type of fluid present after a detected fluid change event based on at least one type of data from the fluid property sensor and send an alert to a fleet manager if the type of fluid is out of specification.

In a fiftieth aspect, in addition to one or more of the preceding or following aspects, or in the alternative to some aspects, the fluid property sensor measures viscosity, density, impedance, dielectric constant, and resistivity of engine fluid.

In a fifty-first aspect, in addition to one or more of the preceding or following aspects, or in the alternative to some aspects, the fluid condition sensing system can be configured to determine a fluid contamination state based on data from the fluid property sensor.

In a fifty-second aspect, in addition to one or more of the preceding or following aspects, or in the alternative to some aspects, the fluid contamination state includes the presence and/or amount of at least one of ingressed contaminants and generated contaminants.

In a fifty-third aspect, in addition to one or more of the preceding or following aspects, or in the alternative to some aspects, the fluid contamination state includes at least one of oxidation state, water contamination, coolant contamination, fuel contamination, soot contamination, metal contamination, total base number value, total acid number value, and incorrect fluid presence.

In a fifty-fourth aspect, in addition to one or more of the preceding or following aspects, or in the alternative to some aspects, the fluid condition sensing system can be configured to determine engine fluid water contamination and coolant contamination when a measured temperature of the fluid is less than 100 degrees Celsius.

In a fifty-fifth aspect, in addition to one or more of the preceding or following aspects, or in the alternative to some aspects, the fluid condition sensing system can be configured to determine engine fluid fuel contamination when a measured temperature of the fluid is less than 110 degrees Celsius.

In a fifty-sixth aspect, in addition to one or more of the preceding or following aspects, or in the alternative to some aspects, the fluid condition sensing system can be configured to determine engine fluid oxidation and soot contamination when a measured temperature of the fluid is from 90 to 125 degrees Celsius.

In a fifty-seventh aspect, in addition to one or more of the preceding or following aspects, or in the alternative to some aspects, the fluid condition sensing system can be configured to classify the engine fluid contamination state as having a slow evolution speed or a high evolution speed.

In a fifty-eighth aspect, in addition to one or more of the preceding or following aspects, or in the alternative to some aspects, the fluid condition sensing system can be configured to classify the engine fluid contamination state using current data reflecting viscosity, density, dielectric constant, and resistivity in comparison with baseline data for the same.

In a fifty-ninth aspect, in addition to one or more of the preceding or following aspects, or in the alternative to some aspects, the fluid condition sensing system can be configured to classify the engine fluid contamination state as being coolant or water contamination if dielectric constant increases, viscosity can be stable, and resistivity decreases.

In a sixtieth aspect, in addition to one or more of the preceding or following aspects, or in the alternative to some aspects, the fluid condition sensing system can be configured to classify the engine fluid contamination state as being fuel dilution if viscosity increases and other parameters are stable.

In a sixty-first aspect, in addition to one or more of the preceding or following aspects, or in the alternative to some aspects, the fluid condition sensing system can be configured to classify the engine fluid contamination state as being soot contamination if viscosity increases and dielectric constant increases.

In a sixty-second aspect, in addition to one or more of the preceding or following aspects, or in the alternative to some aspects, the fluid condition sensing system can be configured to evaluate geolocation data when automatically detecting when the fluid change event has occurred.

In a sixty-third aspect, in addition to one or more of the preceding or following aspects, or in the alternative to some aspects, the fluid can include a hydrocarbon fluid.

In a sixty-fourth aspect, in addition to one or more of the preceding or following aspects, or in the alternative to some aspects, the fluid can include a lubricating oil.

In a sixty-fifth aspect, in addition to one or more of the preceding or following aspects, or in the alternative to some aspects, the fluid can include a hydraulic fluid.

In a sixty-sixth aspect, in addition to one or more of the preceding or following aspects, or in the alternative to some aspects, the fluid can include at least one selected from the group consisting of an engine oil, a transmission fluid, a compressor oil or fluid, and a pump oil or fluid.

In a sixty-seventh aspect, a method of monitoring fluid conditions can be included. The method can include measuring fluid properties with a fluid property sensor, detecting when a fluid change event has occurred based on the measured fluid properties, recording fluid property sensor data as new baseline data after a detected oil change event, and evaluating a condition of a fluid based on a comparison between current fluid property sensor data and the new baseline data.

In a sixty-eighth aspect, in addition to one or more of the preceding or following aspects, or in the alternative to some aspects, the method can further include evaluating whether current fluid property sensor data including at least one of viscosity, density, dielectric constant, and resistivity fall within a predetermined range before the operation of the evaluating a condition of a fluid based on a comparison between current fluid property sensor data and the new baseline data.

In a sixty-ninth aspect, in addition to one or more of the preceding or following aspects, or in the alternative to some aspects, wherein detecting when the fluid change event has occurred includes evaluating signals from the fluid property sensor and interpreting a change in dielectric constant crossing a threshold value as an absolute value, an amount of change as an absolute value, a relative value, or an amount of change as a relative value, as a fluid change event.

In a seventieth aspect, in addition to one or more of the preceding or following aspects, or in the alternative to some aspects, wherein detecting when the fluid change event has occurred includes evaluating signals from the fluid property sensor and interpreting a change in viscosity crossing a threshold value as an absolute value, an amount of change as an absolute value, a relative value, or an amount of change as a relative value, as a fluid change event as a fluid change event.

In a seventy-first aspect, in addition to one or more of the preceding or following aspects, or in the alternative to some aspects, wherein viscosity data can be utilized as a moving average.

In a seventy-second aspect, in addition to one or more of the preceding or following aspects, or in the alternative to some aspects, the method can further include normalizing viscosity data based on temperature data.

In a seventy-third aspect, in addition to one or more of the preceding or following aspects, or in the alternative to some aspects, the fluid property sensor measures dielectric constant of fluid.

In a seventy-fourth aspect, in addition to one or more of the preceding or following aspects, or in the alternative to some aspects, the method can further include evaluating data from a drain plug sensor.

In a seventy-fifth aspect, in addition to one or more of the preceding or following aspects, or in the alternative to some aspects, the method further can include automatically detecting the oil change event by evaluating signals from the fluid property sensor and the drain plug sensor and interpreting a change in viscosity crossing a threshold value that can be correlated with a drain plug removal event as a fluid change event.

In a seventy-sixth aspect, in addition to one or more of the preceding or following aspects, or in the alternative to some aspects, the method further can include automatically detecting the oil change event by evaluating signals from the fluid property sensor and the drain plug sensor and interpreting a change in dielectric constant crossing a threshold value that can be correlated with a drain plug removal event as a fluid change event.

In a seventy-seventh aspect, in addition to one or more of the preceding or following aspects, or in the alternative to some aspects, the method can further include evaluating a condition of a fluid based on a comparison between current fluid property sensor data and the new baseline data only when a current measured temperature falls within a predetermined temperature range.

In a seventy-eighth aspect, in addition to one or more of the preceding or following aspects, or in the alternative to some aspects, the predetermined temperature range can include from 90 to 125 degrees Celsius.

In a seventy-ninth aspect, in addition to one or more of the preceding or following aspects, or in the alternative to some aspects, the method can further include issuing an alert when a current fluid property value differs from a recorded fluid property value by an amount crossing a threshold value.

In an eightieth aspect, in addition to one or more of the preceding or following aspects, or in the alternative to some aspects, the method can further include estimating a time when a fluid change can be needed based on a rate of change of measured fluid property values versus the baseline fluid property values.

In an eighty-first aspect, in addition to one or more of the preceding or following aspects, or in the alternative to some aspects, the method can further include sending an alert when new baseline fluid property data after a fluid change event has occurred differs from a predetermined expected value by a threshold amount.

In an eighty-second aspect, in addition to one or more of the preceding or following aspects, or in the alternative to some aspects, the method can further include identifying a type of oil present after a detected oil change event based on at least one type of data from the fluid property sensor selected from viscosity and dielectric properties and send an alert indicating the type of oil present.

In an eighty-third aspect, in addition to one or more of the preceding or following aspects, or in the alternative to some aspects, the method can further include sending an alert to a fleet manager if the type of oil can be out of specification.

In an eighty-fourth aspect, in addition to one or more of the preceding or following aspects, or in the alternative to some aspects, the fluid property sensor measures viscosity, density, temperature, impedance, dielectric constant, and resistivity of fluid.

In an eighty-fifth aspect, in addition to one or more of the preceding or following aspects, or in the alternative to some aspects, the method can further include determining a fluid contamination state based on data from the fluid property sensor.

In an eighty-sixth aspect, in addition to one or more of the preceding or following aspects, or in the alternative to some aspects, the fluid contamination state includes the presence and/or amount of at least one of ingressed contaminants and generated contaminants.

In an eighty-seventh aspect, in addition to one or more of the preceding or following aspects, or in the alternative to some aspects, the method can further include classifying the fluid contamination state as having a slow evolution speed or a high evolution speed.

In an eighty-eighth aspect, in addition to one or more of the preceding or following aspects, or in the alternative to some aspects, the method can further include classifying the value of each fluid contamination state parameter into one of three categories.

In an eighty-ninth aspect, in addition to one or more of the preceding or following aspects, or in the alternative to some aspects, the method can further include classifying the fluid contamination state using current data reflecting viscosity, density, dielectric constant, and resistivity in comparison with baseline data for the same.

In a ninetieth aspect, in addition to one or more of the preceding or following aspects, or in the alternative to some aspects, the method can further include classifying the fluid contamination state as being coolant or water contamination if dielectric constant increases, viscosity can be stable, and resistivity decreases.

In a ninety-first aspect, in addition to one or more of the preceding or following aspects, or in the alternative to some aspects, the method can further include classifying the fluid contamination state as being fuel dilution if viscosity decreases and other parameters can be stable.

In a ninety-second aspect, in addition to one or more of the preceding or following aspects, or in the alternative to some aspects, the method can further include classifying the fluid contamination state as being soot contamination if viscosity increases and dielectric constant increases.

In a ninety-third aspect, in addition to one or more of the preceding or following aspects, or in the alternative to some aspects, the method can further include evaluating geolocation data when automatically detecting when the oil change event has occurred.

In a ninety-fourth aspect, in addition to one or more of the preceding or following aspects, or in the alternative to some aspects, the method can further include recording fluid property sensor data as new baseline data after a detected oil change event across a range of temperatures.

In a ninety-fifth aspect, in addition to one or more of the preceding or following aspects, or in the alternative to some aspects, wherein recording fluid property sensor data as new baseline data after a detected oil change event across a range of temperatures includes storing the new baseline data in local memory.

In a ninety-sixth aspect, in addition to one or more of the preceding or following aspects, or in the alternative to some aspects, wherein recording fluid property sensor data as new baseline data after a detected oil change event across a range of temperatures includes transmitting the new baseline data for storage in the cloud.

In a ninety-seventh aspect, in addition to one or more of the preceding or following aspects, or in the alternative to some aspects, the fluid can include a hydrocarbon fluid.

In a ninety-eighth aspect, in addition to one or more of the preceding or following aspects, or in the alternative to some aspects, the fluid can include a lubricating oil.

In a ninety-ninth aspect, in addition to one or more of the preceding or following aspects, or in the alternative to some aspects, the fluid can include a hydraulic fluid.

In a one hundredth aspect, in addition to one or more of the preceding or following aspects, or in the alternative to some aspects, the fluid can include at least one selected from the group consisting of an engine oil, a transmission fluid, a compressor oil or fluid, and a pump oil or fluid.

In a one hundred and first aspect, a hydraulic fluid condition sensing system can be included having a control circuit, a temperature sensor in signal communication with the control circuit, and a fluid property sensor in signal communication with the control circuit. The fluid property sensor measures fluid properties including at least an acid number. The hydraulic fluid condition sensing system can be configured to automatically detect when a fluid change event has occurred, record the fluid property sensor data as new baseline fluid property data after a fluid change event has occurred, and evaluate the condition of the fluid based on a comparison with the baseline fluid property data.

In a one hundred and second aspect, in addition to one or more of the preceding or following aspects, or in the alternative to some aspects, the hydraulic fluid condition sensing system can be configured to automatically detect the fluid change event by evaluating signals from the fluid property sensor and interpret a change in acid number crossing a threshold value as an absolute value, an amount of change as an absolute value, a relative value, or an amount of change as a relative value, as a fluid change event.

In a one hundred and third aspect, in addition to one or more of the preceding or following aspects, or in the alternative to some aspects, the sensing system further can include a drain plug sensor, wherein the drain plug sensor can be in signal communication with the control circuit.

In a one hundred and fourth aspect, in addition to one or more of the preceding or following aspects, or in the alternative to some aspects, the drain plug sensor can include a short-range wireless transceiver, wherein the short-range wireless transceiver can be configured to be mounted in a fixed relationship to a drain pan, and a short-range wireless antenna, wherein the short-range wireless antenna can be configured to be mounted on a drain plug.

In a one hundred and fifth aspect, in addition to one or more of the preceding or following aspects, or in the alternative to some aspects, the hydraulic fluid condition sensing system can be configured to issue an alert when a current acid number value differs from a recorded acid number value by an amount crossing a threshold value.

In a one hundred and sixth aspect, in addition to one or more of the preceding or following aspects, or in the alternative to some aspects, the hydraulic fluid condition sensing system can be configured to estimate a time when a fluid change can be needed based on a rate of change of measured acid number values versus the baseline acid number value.

In a one hundred and seventh aspect, in addition to one or more of the preceding or following aspects, or in the alternative to some aspects, the new baseline fluid property data can be stored in memory in electronic communication with the control circuit.

In a one hundred and eighth aspect, in addition to one or more of the preceding or following aspects, or in the alternative to some aspects, the new baseline fluid property data can be sent through a communication network for storage in the cloud.

In a one hundred and ninth aspect, in addition to one or more of the preceding or following aspects, or in the alternative to some aspects, the hydraulic fluid condition sensing system can be configured to send an alert when new baseline fluid property data after a fluid change event has occurred differs from a predetermined expected value by a threshold amount.

In a one hundred and tenth aspect, in addition to one or more of the preceding or following aspects, or in the alternative to some aspects, the hydraulic fluid condition sensing system can be configured to identify a type of fluid present after a detected fluid change event based on at least one type of data from the fluid property sensor selected from acid number and viscosity and send an alert indicating the type of fluid present.

In a one hundred and eleventh aspect, in addition to one or more of the preceding or following aspects, or in the alternative to some aspects, the hydraulic fluid condition sensing system can be configured to identify a type of fluid present after a detected fluid change event based on at least one type of data from the fluid property sensor and send an alert to a fleet manager if the type of fluid can be out of specification.

In a one hundred and twelfth aspect, in addition to one or more of the preceding or following aspects, or in the alternative to some aspects, the hydraulic fluid condition sensing system can be configured to determine a fluid contamination state based on data from the fluid property sensor.

In a one hundred and thirteenth aspect, in addition to one or more of the preceding or following aspects, or in the alternative to some aspects, the fluid contamination state includes the presence and/or amount of at least one of ingressed contaminants and generated contaminants.

In a one hundred and fourteenth aspect, in addition to one or more of the preceding or following aspects, or in the alternative to some aspects, the hydraulic fluid condition sensing system can be configured to evaluate geolocation data when automatically detecting when the fluid change event has occurred.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Identifying a contamination state or condition of a fluid can be important to achieve optimal cost efficiency when considering when to change fluids and/or filters. There is an immediate cost associated with a fluid and fluid filter change, but also a long-term cost associated with not changing fluid and fluid filters due to factors such as the impact of fluid breakdown and/or contamination on the operation and longevity of engine components and parts. Identifying a contamination state or condition of fluid can also be important to determine when a contamination state has reached a sufficiently level such that continued operation of the system risks significant and costly damage.

Systems that can analyze condition of fluid only in an off-vehicle setting are of limited value. As a first issue, such systems cannot provide feedback to a vehicle operator and/or fleet manager in real-time during vehicle operation. As a second issue, trends are inherently harder to identify when data is being gathered only at a limited number of spaced-out discrete points in time.

However, embodiments herein include on-vehicle fluid condition sensing systems and related methods that can be used to accurately detect the contamination state or condition of fluid used by the vehicle in order to provide such information in real-time during vehicle operation.

Further, various embodiments herein can automatically detect when a fluid change event has occurred and then use data gathered immediately thereafter as a baseline reference point to accurately assess changes in the condition or contamination state of the fluid as it is used during continued operation of the vehicle.

In addition, various embodiments herein can also characterize the condition or contamination state of the fluid, including, but not limited to characterizing the oxidation state, water contamination state, coolant contamination state, fuel contamination state, soot contamination state, metal contamination state, total base number value, total acid number value, and incorrect fluid presence.

Figure 1:
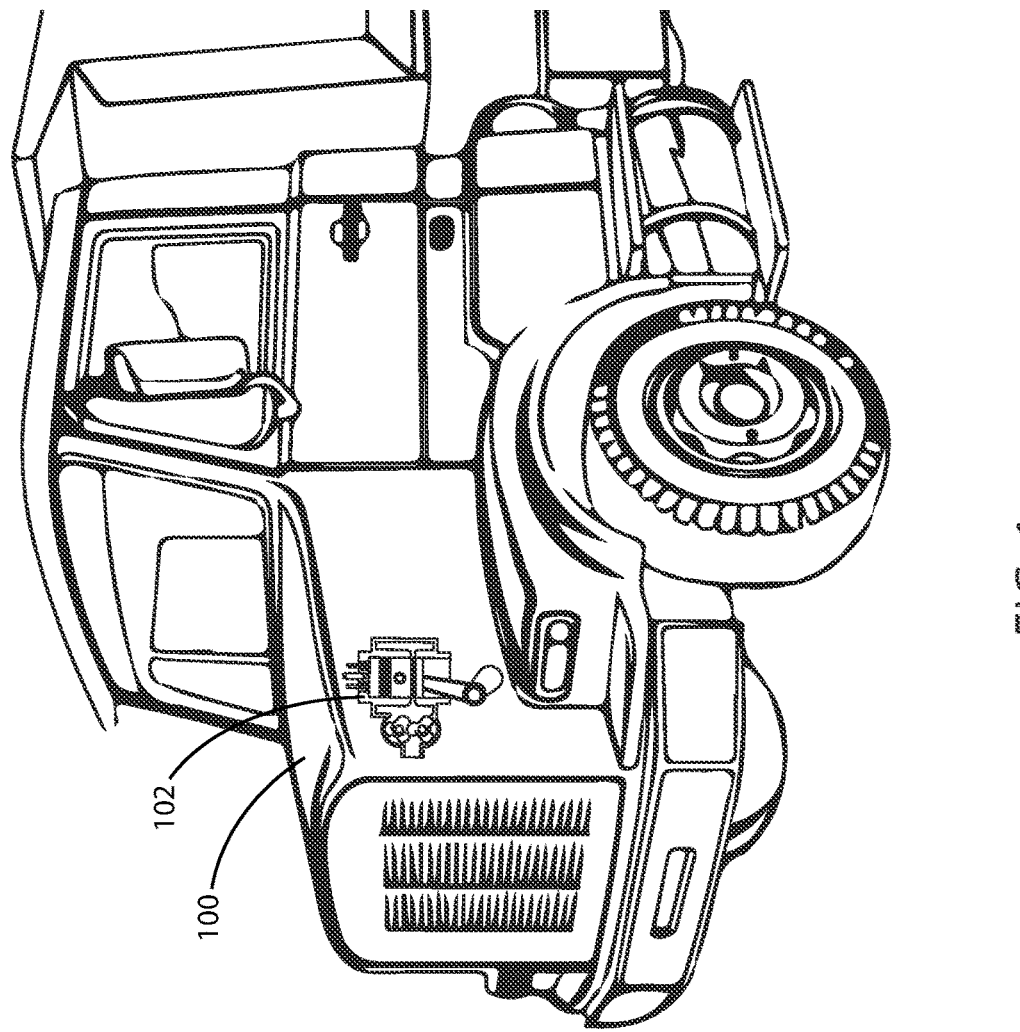
FIG. 1 is a schematic view of a vehicle in accordance with various embodiments herein.
Figure 2:
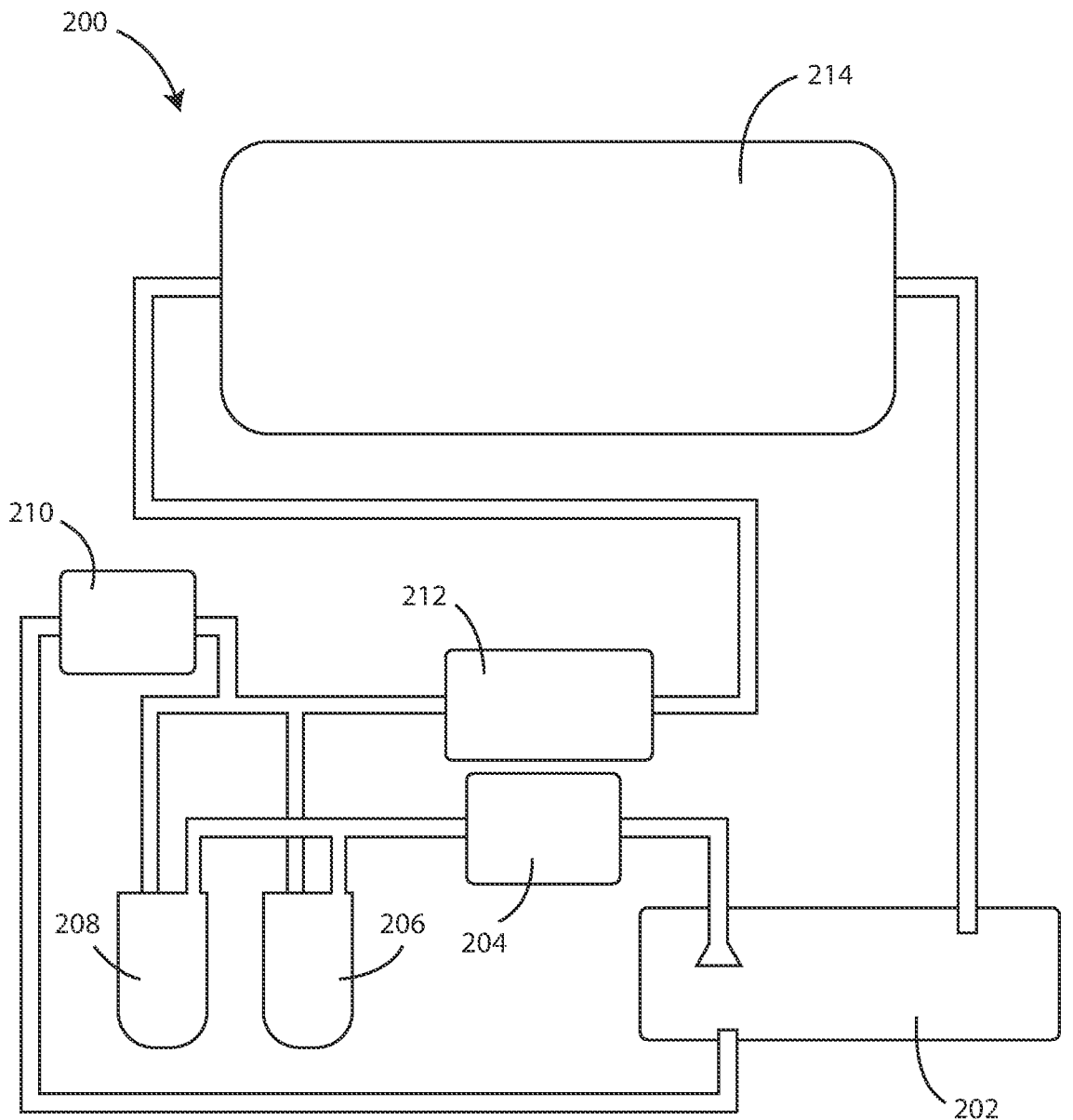
FIG. 2 is a schematic view of a lubrication system in accordance with various embodiments herein.

In some embodiments, engine oils can be monitored using fluid condition sensing systems herein. Referring now to FIG. 1, a schematic view of a vehicle 100 is shown in accordance with various embodiments herein. The vehicle 100 includes an engine 102. The engine 102 includes a lubrication system. Referring now to FIG. 2, a schematic view of an exemplary engine lubrication system 200 is shown in accordance with various embodiments herein. It will be appreciated that the engine lubrication system 200 of FIG. 2 omits various components that may otherwise be a part of an actual lubrication system for ease of illustration. In this view, the engine lubrication system 200 includes an oil pan 202 and an oil pump 204 to draw oil from the oil pan 202. In this specific example, the engine lubrication system 200 also includes a first oil filter 206 and a second oil filter 208, though other numbers of filters (greater or lesser) can also be used. Oil can pass through the oil filters 206, 208 for contaminant removal. In some embodiments, the oil filters can be of a spin-on type of oil filter. However, the oil filters can also be of other types. The engine lubrication system 200 also includes an oil cooler 212. Oil can pass through the oil cooler 212 to have heat removed therefrom. In this example, the engine lubrication system 200 is also shown to pass oil to a turbocharger 210 and well as engine components 214 for the purposes of lubrication, cooling, cleaning, and the like. Oil generally then returns back to the oil pan 202 or reservoir.

Figure 3:
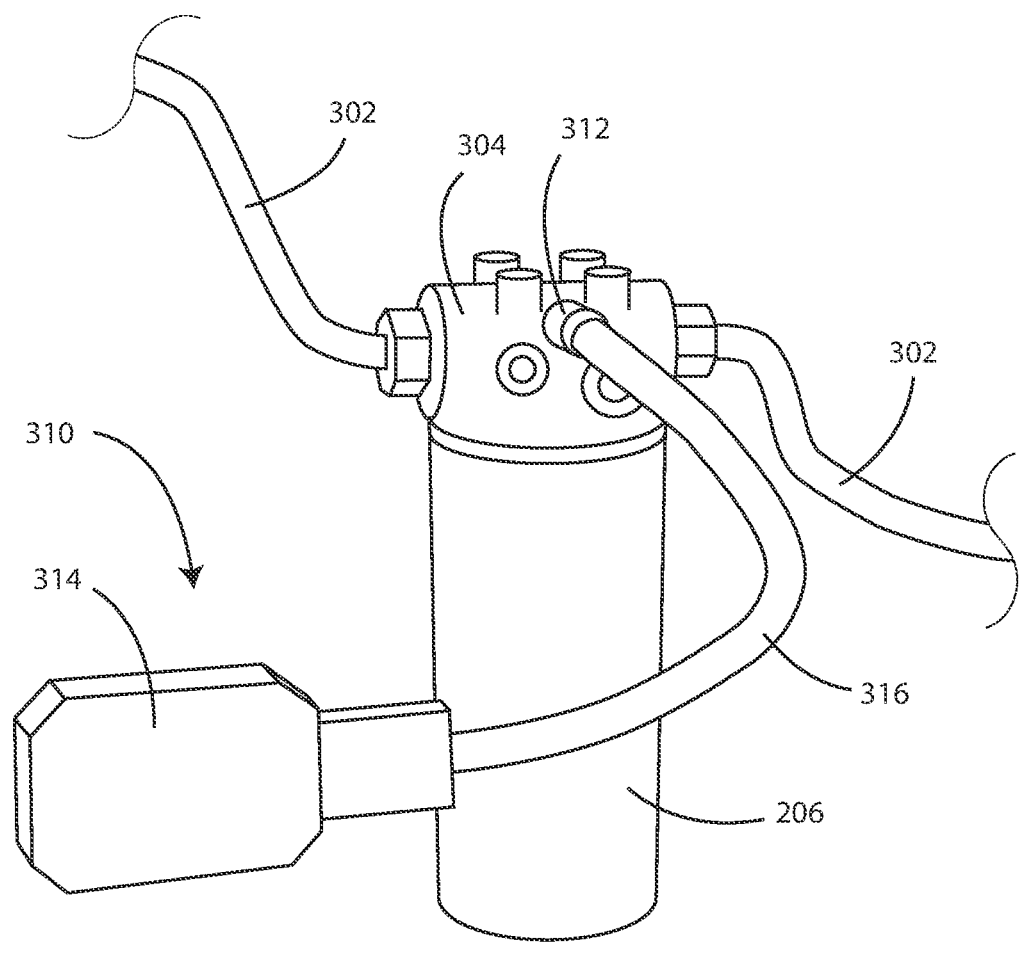
FIG. 3 is a schematic view of an oil condition sensing system in accordance with various embodiments herein.

Referring now to FIG. 3, a schematic view of a fluid condition sensing system 310 is shown in accordance with various embodiments herein. In this view, an oil line 302 is shown leading to and away from the first oil filter 206. The first oil filter 206 fits into a filter head 304 or filter housing. In this example, the fluid condition sensing system 310 includes a fluid property sensor 312 that can fit into the filter head 304. The fluid condition sensing system 310 can also include a housing 314 into which various components fit along with the connection line 316 between the housing 314 and the fluid property sensor 312. While FIG. 3 shows the fluid condition sensing system 310 specifically interfacing specifically with the filter head 304 for the first oil filter 206, it will be appreciated that oil condition sensing systems herein can, in addition or instead, be associated with other oil filters and/or other components of engine lubrication systems. In some embodiments, the fluid property sensor 312 interfaces with the engine oil at another part of the engine lubrication system.

The fluid property sensor 312 can measure a number of different properties of engine oil. In various embodiments, the fluid property sensor 312 can measure one or more of viscosity, density, impedance, dielectric constant, and resistivity of engine 102 oil. In some embodiments, the fluid property sensor can be, at least in part, based on mechanical, electromechanical, electrical, acoustic wave based, resonator, tuning fork, spectroscopy (such as IR or near IR light spectroscopy), optical, or other operative measurement principles. In some cases, the fluid property sensor 312 can include a single sensing element utilizing a measurement principle that can be used to measure or derive multiple fluid properties. For example, a tuning fork-based sensor can measure multiple fluid properties. However, in other cases, the fluid property sensor 312 can include more than one discrete sensing element therein utilizing the same or different sensing properties than other sensing elements. For example, in some cases, the fluid property sensor 312 can be an integrated module including an electromechanical viscosity sensing element and a separate electrically based temperature sensing element. Viscosity sensing elements can include components such as rotational viscosity sensors, linear motion viscosity sensors, tuning fork vibrational sensors, resonator viscosity sensors, quartz crystal wave resonator sensors, acoustic wave viscosity sensors, piezoelectric sensors, spectroscopy sensors, and the like. Dielectric constant sensing elements can include components such as capacitance sensors, time-domain-reflectometry (TDR) sensors, resonant frequency sensors, microwave (and other electromagnetic wave) sensors, and the like. Resistivity sensing elements can include components such as toroidal (inductive) resistivity cells, contact (electrode) resistivity sensors, and the like. In some embodiments, the fluid property sensor 312 can measure the acid number of a fluid (such as with a thermometric sensor).

Some exemplary sensors are described in U.S. Pat. Nos. 6,957,565, 7,043,969; and 9,267,872; the content of which is herein incorporated by reference. Exemplary sensors that can include the FPS2800B12C4 fluid property sensor commercially available from TE Connectivity; the OPS3 C4-A fluid property sensor commercially available from TE Connectivity; the HYDACLab® HLB 1400 commercially available from HYDAC International, GmbH; and the Trident QW3100 oil condition sensor commercially available from Poseidon Systems. A temperature sensor can also be included. Temperature sensors can include components such as a thermistor, thermocouple, resistance temperature detector (RTD), other thermoelectric sensor, or the like. In some embodiments, a thermometric sensor can be included. In some embodiments, an ISFET based sensor can be included.

In various embodiments, the fluid property sensor 312 can be in signal communication with a control circuit, described in greater detail below. The control circuit, alone or in combination with various other components, can perform calculations/operations as described herein.

In various embodiments, the fluid condition sensing system 310 can be configured to automatically detect when an oil change event has occurred. For example, in various embodiments, the fluid condition sensing system 310 can be configured to automatically detect an oil change event by evaluating signals from a fluid property sensor 312 and interpret a change in a fluid property, such as viscosity and/or dielectric constant, as an oil change event. In various embodiments, the fluid condition sensing system 310 can be configured to automatically detect an oil change event by evaluating signals from a fluid property sensor 312 and interpret a change in a fluid property, such as viscosity and/or dielectric constant, crossing a threshold value as an oil change event. Threshold values can be an absolute value, an amount of change as an absolute value, a relative value, or an amount of change as a relative value.

In various embodiments, the fluid condition sensing system 310 can be configured to automatically detect an oil change event by evaluating signals from a fluid property sensor 312 and interpret, specifically, a step change in a fluid property, such as viscosity and/or dielectric constant, as an oil change event. In various embodiments, the fluid condition sensing system 310 can be configured to automatically detect an oil change event by evaluating signals from a fluid property sensor 312 and interpret, a step change simultaneously in one, two, three, or more different fluid properties, such as viscosity, dielectric constant, or viscosity and dielectric constant as an oil change event. A "step change" herein can include a change in a property that exceeds a threshold value (such as a change greater than 5, 10, 15, 20, 25, 30, 40, or 50 percent, or a change exceeding an amount as an absolute value, etc.) in less than a fixed period of time or a fixed period of vehicle operation time (such as less than or equal to 10, 8, 5, 3, 2, or 1 minutes).

In some embodiments, the system can recognize that an oil change event has occurred by executing a pattern matching or classification operation. For example, the system can match current data from the fluid property sensor against a series of stored patterns to determine which is the closest match. The stored patterns can reflect scenarios where an oil change event has occurred as well as scenarios where an oil change event has not occurred. If the closest match for the current data is a pattern reflecting a scenario where an oil change event has occurred, then the system can treat the observed current data as reflecting that an oil change event has in fact occurred. Further details regarding pattern matching operations/techniques are described in greater detail below.

In some embodiments, the system can query an individual or another system to determine and/or confirm whether an oil change event has occurred. For example, the system can initiate a query to be presented to a vehicle operation, a vehicle maintenance specialist, a fleet manager, or the like to confirm whether an oil change event has occurred. In some embodiments herein, after the system automatically detects what is believed to be an oil change event, a query is generated for an individual or system for confirmation.

In various embodiments, the fluid condition sensing system 310 can be configured to record data as new baseline data after an oil change event has been detected. For example, in various embodiments, the fluid condition sensing system 310 can be configured to record fluid property sensor 312 data as new baseline fluid property data after an oil change event has occurred. The baseline data can then be later used to characterize a current state of the oil by way of comparison. For example, in various embodiments, the fluid condition sensing system 310 can be configured to evaluate the condition of an engine oil based on a comparison with the baseline fluid property data.

It will be appreciated that temperature can impact various fluid properties including viscosity. Further, the vehicle may operate with the oil at a range of temperatures and therefore it can be important to control for the impact of temperature on measured properties and/or conclusions drawn therefrom. For example, when a vehicle is first started up, assuming it was shut down long enough to thermally equilibrate with its surroundings, the temperature of the oil will generally be far lower than it is after the engine has fully warmed up and is in use during vehicle operation. However, temperature may also vary during ongoing operations. For example, temperature may be impacted based on the engine load as well as other factors.

However, systems herein can mitigate the effects of changing fluid properties based on temperature change in various ways. In some embodiments, the fluid condition sensing system 310 can be configured to utilize viscosity sensor data only when a measured temperature falls within a predetermined temperature range. In various embodiments, the fluid condition sensing system 310 can be configured to normalize viscosity data based on temperature data. Exemplary techniques of normalizing engine oil viscosity data are described in greater detail below.

In various embodiments, the fluid condition sensing system 310 can be configured to provide information to individuals (such as a driver, fleet manager, or the like) and/or other systems regarding fluid properties that it observes. In various embodiments, the fluid condition sensing system 310 can specifically be configured to issue an alert when a fluid property value differs from a predetermined value by an amount crossing a threshold value. As a specific example, in various embodiments, the fluid condition sensing system 310 can be configured to issue an alert when a current viscosity value differs from a predetermined viscosity value by an amount crossing a threshold value. Thresholds herein can exist as absolute or relative values. In some embodiments, the thresholds can be for example, an absolute value of viscosity or any of the other parameters discussed herein, a particular amount of change in the viscosity or another parameter discussed herein (as an absolute value for change or a relative value for change such as a percentage change), or another type of threshold value. In some embodiments the thresholds can be predetermined and fixed and in other embodiments they can be dynamically determined. In some embodiments, the thresholds can specifically be a percentage change with respect to and established baseline value. For example, in some embodiments, the threshold can be greater than or equal to 5 percent, 10 percent, 15 percent, 20 percent, 25 percent, 30 percent, 35 percent, 40 percent, 45 percent, or 50 percent with respect to a baseline value, or can be an amount falling within a range between any of the foregoing.

In various embodiments, the fluid condition sensing system 310 can be configured to estimate a time when an oil change is needed based on a rate of change of measured viscosity values versus the baseline viscosity value. In some embodiments, the system can extrapolate based on observed trends in one or more fluid properties to estimate when such values will reach a threshold value (which can be predetermined, input by a system user, etc.) that can be used as an indicator that an oil change is recommended. In some embodiments, estimates can be provided in terms of a number of hours (or other unit of time) of operation until an oil change is recommended. In some embodiments, estimates can be provided in terms of a number of miles traveled until an oil change is recommended. In some embodiments, estimates can be provided in terms of a cost curve showing at what point oil should be changed to minimize overall costs.

In various embodiments, the fluid condition sensing system 310 can be configured to send an alert when new baseline fluid property data, gathered after an oil change event has occurred, differs from a predetermined expected value by a threshold amount. If the baseline fluid property data is different than what would be expected, this can indicate a problem such as the wrong type of oil (and/or wrong type of fluid) being added.

In various embodiments, the fluid condition sensing system 310 can be configured to identify a type of oil present after a detected oil change event based on at least one type of data from a fluid property sensor 312 selected from viscosity and dielectric properties and send an alert indicating the type of oil present. In various embodiments, the fluid condition sensing system 310 can be configured to identify a type of oil present after a detected oil change event based on at least one type of data from the fluid property sensor 312 and send an alert to a fleet manager if the type of oil is out of specification.

Oil or fluid type can be identified based on the measured fluid properties. For example, the viscosity and dielectric constant are properties that can vary depending on the particular type of oil. As a specific example of this, an unused SAE 15W-40 oil has a higher viscosity at 100 degrees Celsius than does an unused SAE 5W-30 oil. In various embodiments, if new baseline fluid property values established after an oil change event are inconsistent with that which is expected then an alert can be issued regarding the presence of an out-of-specification oil. Similarly, if new baseline fluid property values established after an oil change event are different than the previous set of baseline fluid property values (e.g., those established after the previous oil change event) then an alert can be issued by the system.

In various embodiments, the fluid condition sensing system 310 utilizes fluid state parameters as absolute instantaneous values. However, in some embodiments, the fluid condition sensing system 310 utilizes fluid state parameters as a moving average. For example, in some embodiments, the fluid condition sensing system 310 uses dielectric constant values as absolute instantaneous values. However, in some embodiments, the fluid condition sensing system 310 uses viscosity data as a moving average.

In various embodiments, the fluid condition sensing system 310 can be configured to determine an engine oil contamination state based on data from the fluid property sensor 312. For example, the engine oil contamination state can include at least one of oxidation state, water contamination, coolant contamination, fuel contamination, soot contamination, metal contamination, total base number value, total acid number value, and incorrect fluid presence. In some embodiments, the fluid contamination state includes the presence and/or amount of at least one of ingressed contaminants and generated contaminants. Ingressed contaminants can include at least one of water contamination, air contamination, chemical contamination, particulates, biological contaminants, oil heat contaminants, and the like. Generated contaminants can include oxidation products, wear contaminants (such as rubber and metal contaminants), and the like.

Figure 4:
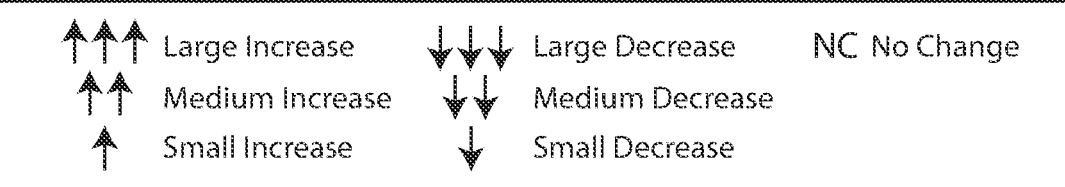
FIG. 4 is a view of oil contamination states in accordance with various embodiments herein.

Referring now to FIG. 4, a view of oil contamination states is shown in accordance with various embodiments herein. In various embodiments, the fluid condition sensing system 310 can be configured to classify the engine oil contamination state using current data reflecting viscosity, density, dielectric constant, and resistivity in comparison with baseline data for the same.

FIG. 4 shows expected changes to viscosity, density, dielectric constant, and resistivity with respect to baseline values for different engine oil contamination states. References herein to viscosity shall refer to dynamic viscosity (cP) unless otherwise specified or unless the context dictates otherwise. Classifications of engine oil contamination can be based upon changes over baseline in one or more of these parameters. For example, in various embodiments, the fluid condition sensing system 310 can be configured to classify the engine 102 oil contamination state as being coolant or water contamination if dielectric constant increases, viscosity is stable, and resistivity decreases. In various embodiments, the fluid condition sensing system 310 can be configured to classify the engine 102 oil contamination state as being fuel dilution if viscosity decreases and other parameters are stable. In various embodiments, the fluid condition sensing system 310 can be configured to classify the engine 102 oil contamination state as being soot contamination if viscosity increases and dielectric constant increases. In various embodiments, the fluid condition sensing system 310 can be configured to classify the engine 102 oil contamination state as being oxidation if viscosity increases, dielectric constant is stable, and resistivity is stable.

Classification of oil contamination states can be performed across a wide range of temperatures. In some embodiments, classification of oil states is performed within a more limited window of, for example, 90 to 125 degrees Celsius. However, when considering specific types of contamination, there can be advantages to evaluating the same at specific temperatures or temperature ranges. For example, there can be an advantage in evaluating water or coolant contamination at temperatures of less than 100 degrees Celsius (less than the boiling temperature of water at the site of the system with the oil as may be impacted by pressure, altitude, etc.) so that the water does not boil away. As such, in various embodiments, the fluid condition sensing system 310 can be configured to evaluate the engine oil contamination states of water contamination and coolant contamination when a measured temperature of the oil is less than 100 degrees Celsius, such as from 0 to 99 degrees Celsius or from 10 to 99 degrees Celsius, or at a temperature less than less than a boiling temperature of water at a location of the oil being evaluated, or the like. In contrast, in some embodiments, the fluid condition sensing system 310 can be configured to determine the engine oil oxidation state or soot contamination when a measured temperature of the oil is from 90 to 125 degrees Celsius. As another example, fuel contamination can be beneficially measured at temperatures wherein the absolute difference between the viscosity of oil and fuel is increased, such as at temperature that are less than 110, 100, 90, 80, 70, 60, or 50 degrees Celsius or less.

In various embodiments, the fluid condition sensing system 310 can be configured to classify the engine 102 oil contamination state as having a slow evolution speed or a high evolution speed. For example, the system can assess how rapidly has the contamination state progressed and classify the contamination state accordingly. This information can be included with outputs such as alerts or other information provided to other systems and/or individuals such as a driver or a fleet manager. For example, if a particular contamination state is observed to be rapidly getting worse this can pose a greater risk to the vehicle through continued operation and result in a more urgent need for vehicle service. As a specific example, rapidly progressing coolant contamination may result from cracked cylinder heads, blown heat gaskets, defective seals, cracked manifolds or the like and may present an urgent need for service. In various embodiments herein, the system can send an alert to a vehicle operator, a fleet manager, or another individual informing them of an urgent need for service or ceasing vehicle operation if rapidly progressing coolant contamination (or another rapidly progression contamination state) has been detected.

While FIG. 4 exemplifies contamination states for an oil such as an engine oil, it will be appreciated that many different types of oils/fluids can be monitored using fluid condition sensing systems herein. By way of example, fluid condition sensing systems herein can be used to evaluate/monitor various types of hydrocarbon fluids. By way of example, fluid condition sensing systems herein can be used to evaluate/monitor various types of lubricating oils. Fluid condition sensing systems herein can also be used to evaluate/monitor various hydraulic fluids/oils. In some embodiments, systems herein can be used to monitor at least one fluid selected from the group consisting of an engine oil, a transmission fluid, a compressor oil or fluid, a pump oil or fluid, and the like.

In some embodiments, the fluid contamination state includes the presence and/or amount of at least one of ingressed contaminants and generated contaminants. Ingressed contaminants can include at least one of water contamination, air contamination, chemical contamination, particulates, biological contaminants, oil heat contaminants, and the like. Generated contaminants can include oxidation products, wear contaminants (such as rubber and metal contaminants), and the like.

In some cases, the parameters evaluated may change depending on the type of oil or fluid being evaluated or monitored. For example, fresh hydraulic fluid or oil may have an acid number (AN) of around 0.2 mg KOH/g. However, this will generally increase over time (due to oxidation reactions and other mechanisms). Once the oil has a value such as 1.2, 1.4, 1.6, 1.8, or 2 mg KOH/g or greater, then a fluid change would be recommended. After the fluid change, then the measured acid number will fall down to the level of new hydraulic fluid or oil. Thus, systems herein can use acid number to detect fluid changes, such as in the context of hydraulic fluids or oils. Similarly, systems herein can use acid number to condition and/or contamination state of hydraulic fluids or oils.

Figure 5:
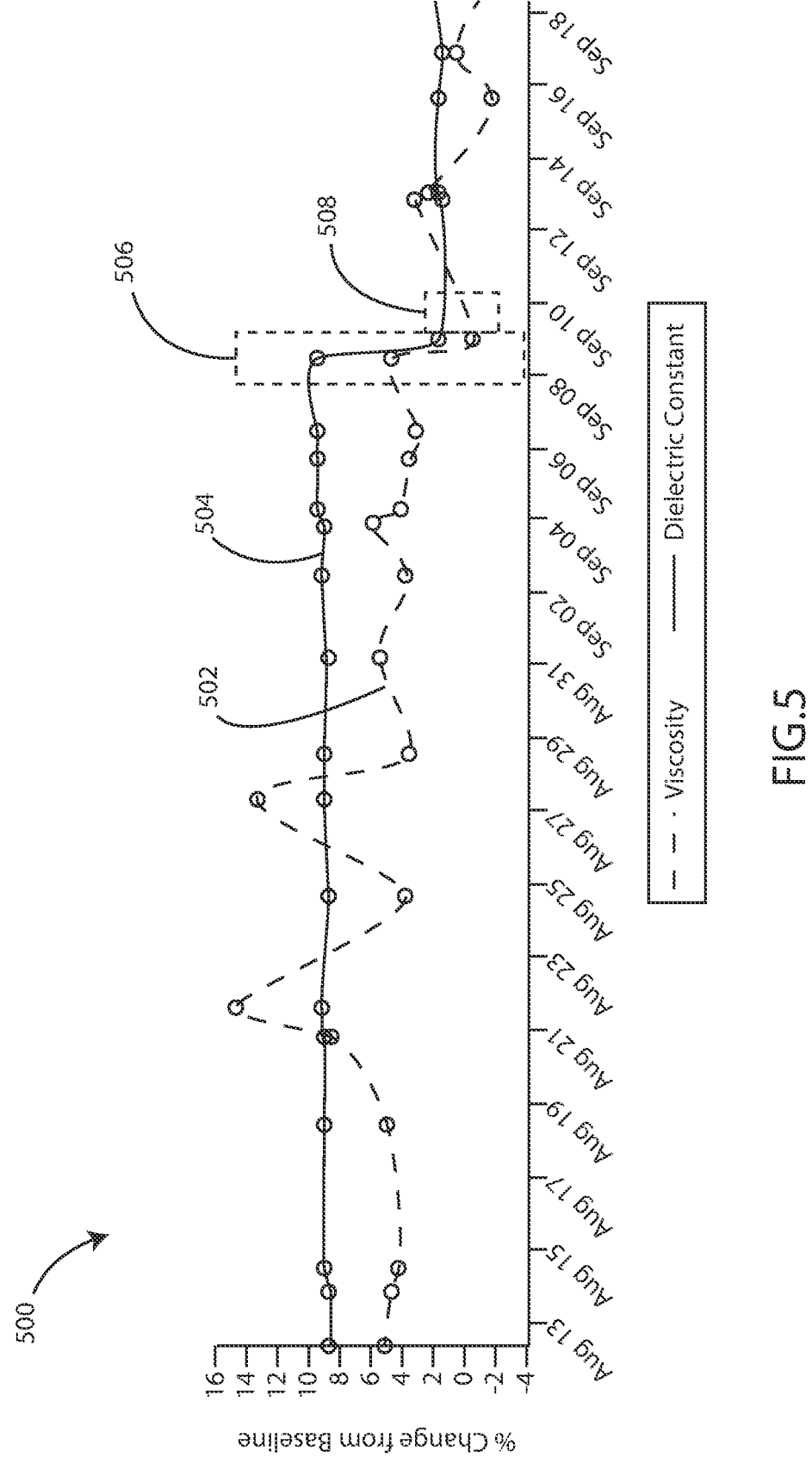
FIG. 5 is a graph of oil viscosity and dielectric constant over time in accordance with various embodiments herein.

Establishing baseline values for fluid properties can be critical to detecting fluid contamination states. Referring now to FIG. 5, a graph 500 of oil viscosity and dielectric constant over time is shown in accordance with various embodiments herein. The graph 500 includes a viscosity curve 502 and a dielectric constant curve 504. Both viscosity and dielectric constant exhibit a step change at the time of an oil change event 506. New baseline values can be gathered at time 508 immediately after the oil change event 506.

In various embodiments, the fluid condition sensing system 310 can be configured to automatically detect the oil change event 506 by evaluating signals from the fluid property sensor 312 and interpret a change in viscosity crossing a threshold value as an oil change event 506.

In various embodiments, the fluid condition sensing system 310 can be configured to automatically detect the oil change event 506 by evaluating signals from the fluid property sensor 312 and interpret a change in dielectric constant values crossing a threshold value as an oil change event 506.

As referenced above, it will be appreciated that some fluid property values are substantially impacted by temperature. Therefore, accommodating variations in temperature can be important in interpreting observed fluid property values otherwise changes in certain properties such as viscosity may be misinterpreted. In various embodiments, the oil condition sensing system herein can be configured to normalize viscosity data and/or other types of fluid property data based on temperature data. This can be done in various ways by the system herein.

In some embodiments the system can (for each data point) first convert viscosity data from dynamic viscosity (cP) to kinematic viscosity (cSt) by dividing by the density. The system can normalize the kinematic viscosity to a desired temperature, for example 100° C., by the following method. It will be appreciated, however, that normalizing to other temperatures can also be performed in accordance with embodiments herein using the same approach. The system can then calculate the Walther viscosity as log 10(log 10($\mu$+0.7)) where $\mu$ is the kinematic viscosity. The system can then calculate the Walther viscosity correction according to the following equation (Equation 1):

$$\text{Walther viscosity correction=slope*(log 10(100° C.+273.15)–log 10(}T\text{+273.15))}$$

wherein the slope is calculated from a linear fit of the uncorrected viscosity vs. temperature data as plotted on a log-log plot with a Y axis of log 10(log 10($\mu$+0.7)) and an X axis of log 10(T) and T is the temperature in ° C.

Next, the system can apply the Walther viscosity correction according to the following equation (Equation 2):

$$\text{Temperature Corrected Walther viscosity=Walther viscosity+Walther viscosity correction}$$

Next, the system can calculate the temperature-corrected viscosity from the temperature corrected Walther viscosity according to the following equation (Equation 3):

$$\text{Temperature corrected viscosity=10}^{\wedge}\text{(10}^{\wedge}\text{temperature corrected Walther viscosity)–0.7}$$

Other approaches for temperature-based normalization of viscosity and other fluid property values can also be used. In some embodiments, a set of values for a given fluid property over a range of temperatures can be stored in the system and then the control circuit can estimate a temperature-corrected value for a current measured value using an interpolation procedure referencing the stored set of values.

In some embodiments, temperature-based normalization of dielectric constant values can be performed by the system herein. In some embodiments, the system is configured to normalize dielectric constant values for temperature with a linear or simple polynomial fit-based temperature correction.

Figure 6:
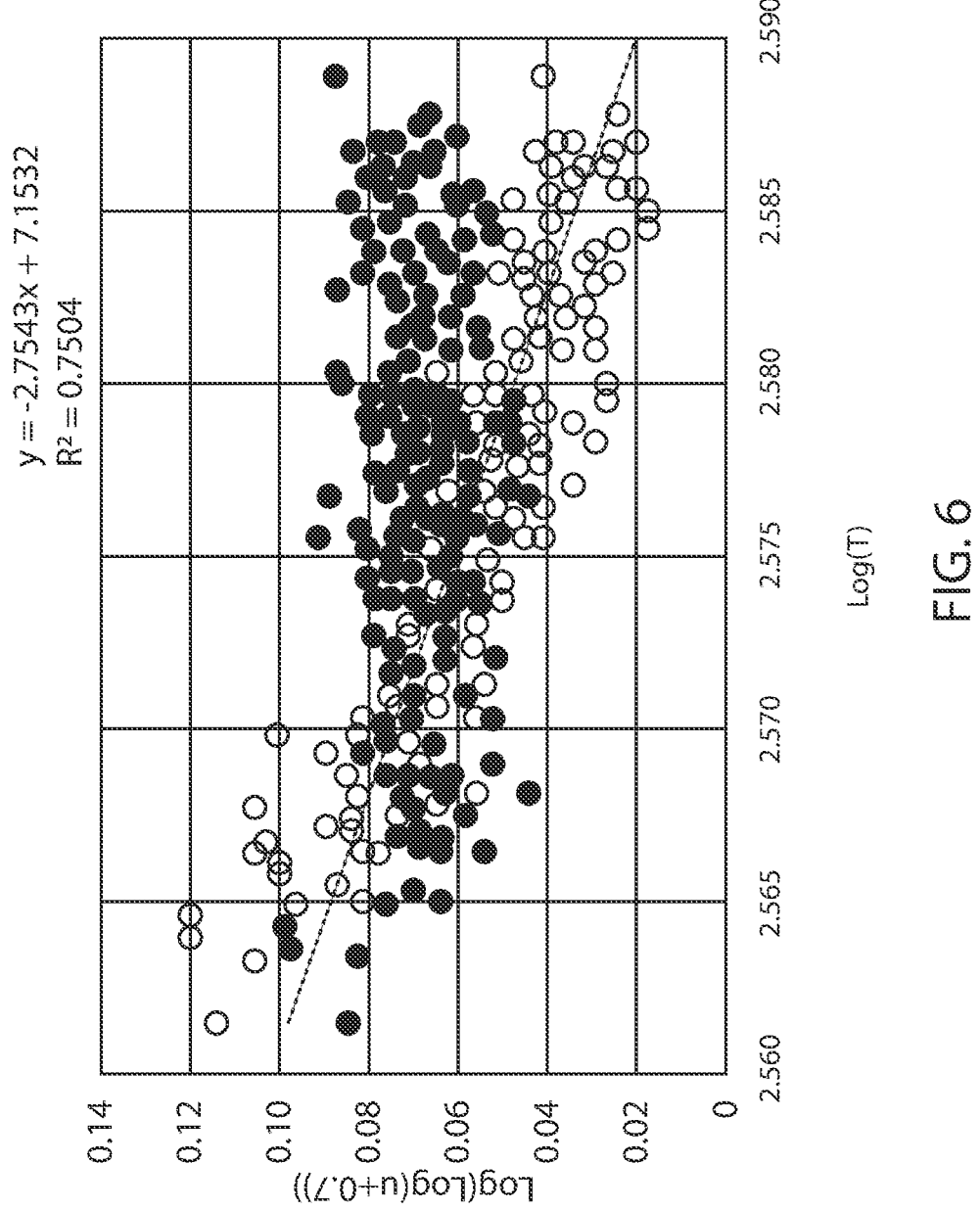
FIG. 6 is a graph of measured viscosity and viscosity as corrected for temperature in accordance with various embodiments herein.

Referring now to FIG. 6, a graph of measured viscosity and viscosity as corrected for temperature is shown in accordance with various embodiments herein. FIG. 6 illustrates how the system can account for variations in temperature such that fluid property values, such as viscosity, are correctly interpreted. In particular, FIG. 6 shows a series of uncorrected viscosity values. As can be seen, these exhibit a trend of decreasing viscosity with increasing temperature as would be expected. FIG. 6 also show a series of corrected viscosity values that have been calculated using the technique described above. These data points exhibit substantially constant viscosity values over a temperature range from below 95 degrees Celsius to 110 degrees Celsius.

In various embodiments, the fluid condition sensing system 310 can be configured to utilize viscosity sensor data only when a measured temperature falls within a predetermined temperature range. In various embodiments, the predetermined temperature range can include from 90 to 125 degrees Celsius.

Figure 7:
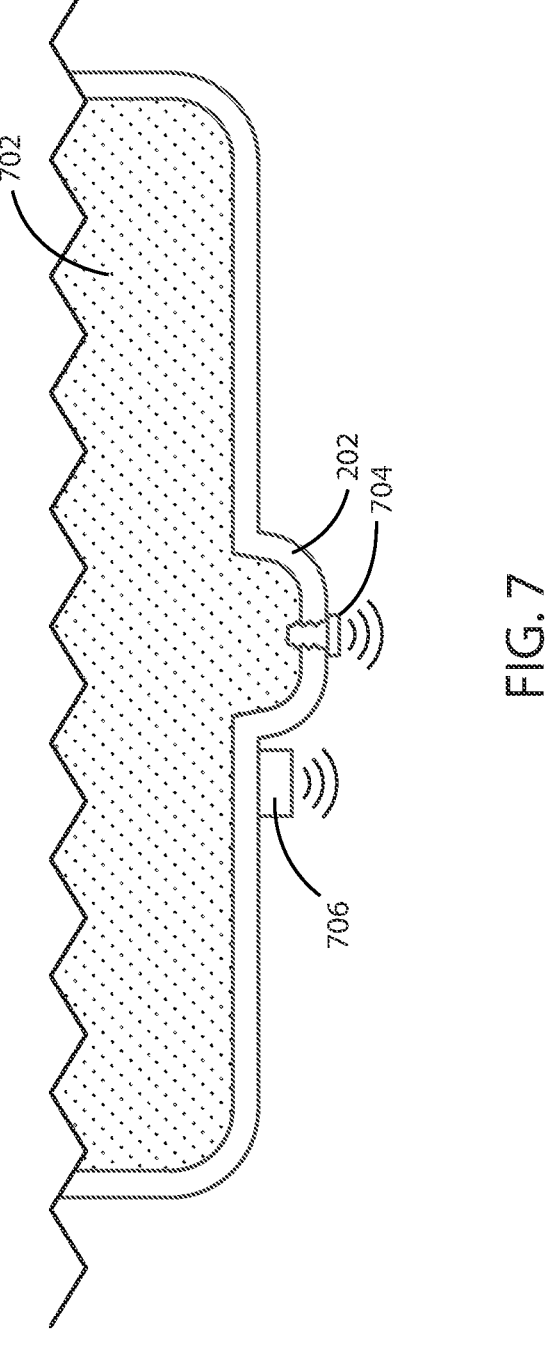
FIG. 7 is a schematic view of an oil pan and oil plug sensor system in accordance with various embodiments herein.

In some embodiments, an oil plug sensor can be utilized to detect an oil change event or confirm automatic detection of the same. Referring now to FIG. 7, a schematic view of an oil pan 202 and oil plug sensor 706 system is shown in accordance with various embodiments herein. FIG. 7 shows an oil 702 within the oil pan 202. An oil drain plug 704 fits within an aperture in the bottom of the oil pan 202. The engine lubrication system also includes an oil plug sensor 706.

The drain plug sensor can be configured to operation in various ways. In some embodiments, the drain plug sensor can include a short-range wireless reader that can be mounted in a fixed relationship to the oil pan 202. The oil drain plug 704 itself can be fitted with a short-range wireless tag.

The short-range wireless reader can be configured to wirelessly send data to and receive data from the short-range wireless tag when the short-range wireless reader and the short-range wireless tag are at a distance that is less than or equal to a maximum communication distance. Thus, when the short-range wireless reader and short-range wireless tag can communicate with one another it can be concluded that the oil drain plug 704 is mounted in the drain aperture of the oil pan 202.

However, removal of the drain plug from the oil pan 202 can cause movement of the short-range wireless tag away from the short-range wireless reader by an amount that causes the distance between the short-range wireless tag and the short-range wireless reader to exceed the maximum communication distance. Thus, the oil plug sensor 706 can detect the removal of the oil drain plug 704 by noting a loss of communication with the short-range wireless tag of the oil drain plug 704 as it is moved out of the fixed maximum transmission range of the short-range wireless reader during the process of changing oil on the vehicle.

In some embodiments, the short-range wireless communication components herein are, specifically, near-field communication (NFC) components. For example, the short-range wireless communication tag can be a near-field communication (NFC) tag. The short-range wireless communication reader can be a near-field communication (NFC) reader.

Near-field wireless communication employs electromagnetic induction between two loop antennas when NFC-enabled devices or components exchange information. Generally, NFC devices operate within the globally available unlicensed radio frequency ISM band of 13.56 MHz on ISO/IEC 18000-3 air interface at rates ranging from 106 to 424 Kbit/s.

NFC devices can operate in various modes, including NFC card emulation, NFC reader/writer, and NFC peer-to-peer. In various embodiments, NFC devices herein are operating in reader/writer mode, which NFC-enabled devices to read information stored on NFC tags embedded in or disposed on filter elements.

In accordance with various embodiments herein, tags can be passive data stores which can be read, and under some circumstances written to, by a device, such as a reader device. They typically contain data (in some cases between 96 and 8,192 bytes). In some embodiments the tags are read-only, but in some embodiments they can be rewritable. In some embodiments, a tag in accordance with embodiments herein can include an antenna consisting of a coil of wire and an integrated circuit (IC) which can include memory circuits for data storage. In various embodiments, the tag can also include a capacitor. The reader typically has its own antenna, which can continuously or intermittently transmit a short-range radio frequency field.

When the tag is placed within range of the reader, the antenna coil and capacitor, which form a tuned circuit, absorb and store energy from the field, resonating like an electrical version of a tuning fork. This energy can be rectified to direct current which powers the integrated circuit. The integrated circuit can send its data to the antenna coil, which transmits it by radio frequency signals back to the reader unit. Since all the energy to power the tag comes from the reader unit, the tag must be close to the reader to function. Therefore, communication between the tag and the reader only has a limited range.

The distance for short-range wireless communication in embodiments herein can vary. In some embodiments, steps can be taken to purposefully limit the range of short-range wireless communication including, but not limited to, varying the size of the antenna coil, limiting the power associated with the emission of the radio frequency field, and the like. In some embodiments, the maximum short-range wireless communication distance is less than 12, 10, 8, 7, 6, 5, 4, 3, or 2 inches. In some embodiments, the maximum short-range wireless communication distance is within a range wherein any of the foregoing can serve as the upper or lower bound of the range. In some embodiments, the maximum short-range wireless communication distance is less than 30, 25, 20, 18, 16, 14, 12, 10, 8 or 6 centimeters.

It will be appreciated, however, that that system illustrated with respect to FIG. 7 is merely one example of how an oil plug sensor 706 could work. In some embodiments, the sensor can be configured so that a conductive loop includes the oil drain plug 704 and when it is removed the circuit opens, which can be detected by the oil plug sensor 706. Thus, in some embodiments, the oil plug sensor 706 can function using wireless techniques and in other embodiments can function using wired approaches. The oil plug sensor 706 can be in signal communication with the control circuit of the system.

In various embodiments, the fluid condition sensing system 310 can be configured to automatically detect an oil change event by evaluating signals from the fluid property sensor and the drain plug sensor and interpret a change in viscosity crossing a threshold value that is correlated with a drain plug removal event as an oil change event.

Figure 8:
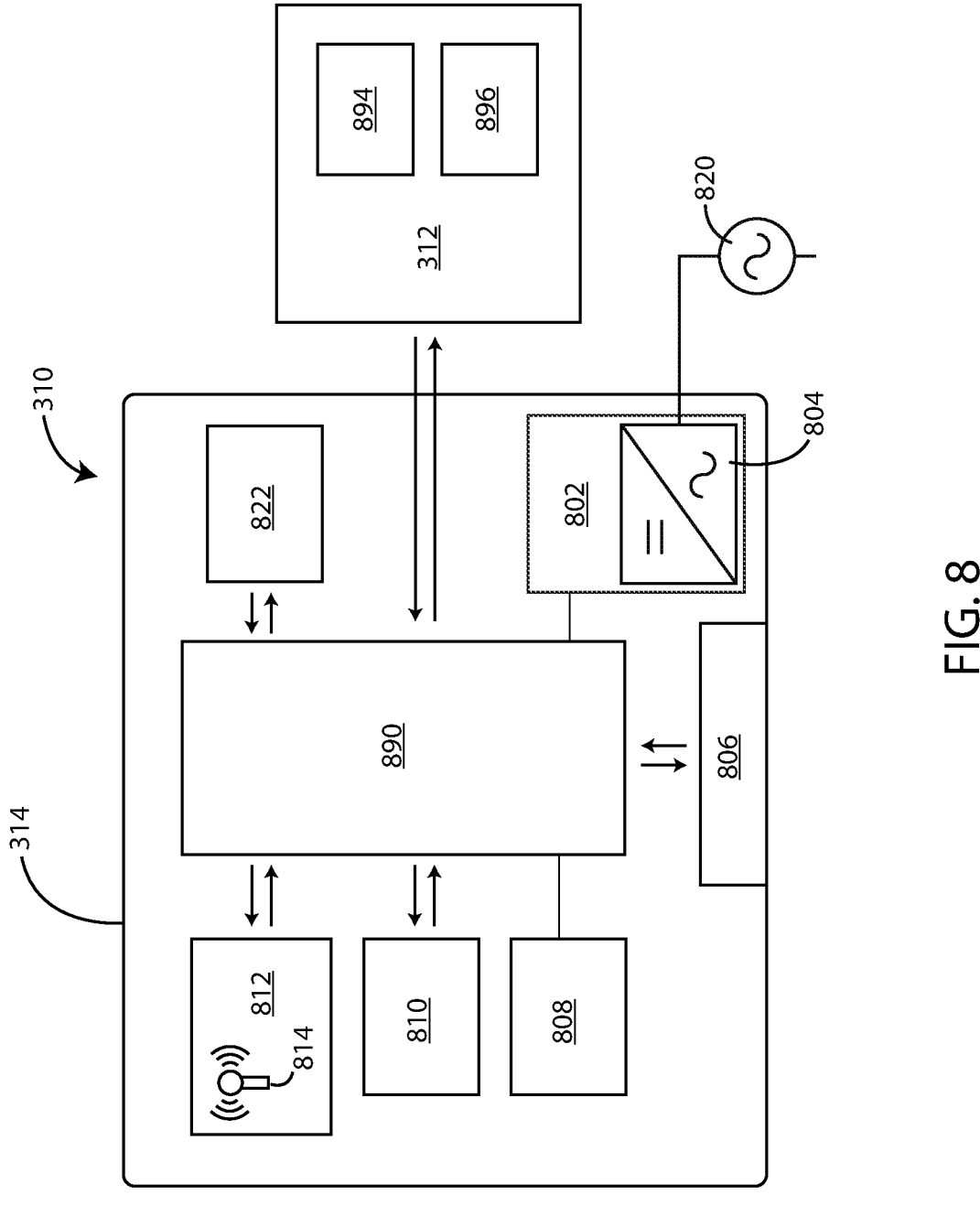
FIG. 8 is a schematic view of components of an oil condition sensing system in accordance with various embodiments herein.

Referring now to FIG. 8, a schematic view of components of a fluid condition sensing system 310 is shown in accordance with various embodiments herein. It will be appreciated, however, that a greater or lesser number of components can be included with various embodiments and that this schematic diagram is merely illustrative.

In this example, the condition sensing system 310 can include a fluid property sensor 312 and a housing 314. The fluid property sensor 312 can include a first sensing element 894, which can be a tuning fork-based sensing element for measuring viscosity, density, dielectric constant, and optionally resistivity. In this example, the fluid property sensor 312 can also include a second sensing element 896, which can be a temperature sensor. It will be appreciated that a greater or lesser number of sensing elements can be used. Sensing elements can include any of those described elsewhere herein.

A control circuit 890 can be disposed within the housing 314. The control circuit 890 can include various electronic components including, but not limited to, a microprocessor, a microcontroller, a FPGA (field programmable gate array) chip, an application specific integrated circuit (ASIC), or the like. The processing power of the control circuit 890 and components thereof can be sufficient to perform various operations including various operations on data from sensors including, but not limited to averaging, time-averaging, statistical analysis, normalizing, aggregating, sorting, deleting, traversing, transforming, condensing (such as eliminating selected data and/or converting the data to a less granular form), compressing (such as using a compression algorithm), merging, inserting, time-stamping, filtering, discarding outliers, calculating trends and trendlines (linear, logarithmic, polynomial, power, exponential, moving average, etc.), predicting oil and/or filter EOL (end of life), identifying an EOL condition, predicting performance, predicting costs associated with replacing oil and/or filter elements vs. not-replacing oil and/or filter elements, and the like.

Normalizing operations performed by the control circuit 890 can include, but are not limited to, adjusting one or more values based on another value or set of values. As just one example, viscosity data can normalized by accounting for temperature as described elsewhere herein.

In various embodiments the control circuit 890 can calculate a time for replacement of oil and/or an oil filter element and generate a signal regarding the time for replacement. In various embodiments, the control circuit can calculate a time for replacement of oil and/or an oil filter element and issue a notification regarding the time for replacement through a user output device. In various embodiments, control circuit issue an alert if a predetermined alert or alarm condition has been met.

In various embodiments, the fluid property sensor 312 can include a power supply circuit 802 disposed within the housing 314. In some embodiments, the power supply circuit 802 can include various components including, but not limited to, a rectifier 804, a capacitor, a power-receiver such as a wireless power receiver, a transformer, a battery, and the like. In some embodiments, the power supply circuit 802 can be in electrical communication with a source of power 820. The source of power 820 can either be an AC or DC power source, with implications for the other components of the power supply circuit 802 (such as a rectifier 804 typically not being needed when the source of power 820 is DC).

In some embodiments the condition sensing system 310 can include an output device 806 disposed on the housing 314. The output device 806 can include various components for visual and/or audio output including, but not limited to, lights (such as LED lights), a display screen, a speaker, and the like. In some embodiments, the output device can be used to provide notifications or alerts to a system user such as current system status, an indication of a problem, a required user intervention, a proper time to perform a maintenance action, or the like. It will be appreciated, however, that in various embodiments notifications and/or alerts can be provided electronically to another device or component, such as a vehicle system, a remote system, a driver device, or the like.

In various embodiments the condition sensing system 310 can include memory 808 and/or a memory controller disposed within the housing 314. The memory can include various types of memory components including dynamic RAM (D-RAM), read only memory (ROM), static RAM (S-RAM), disk storage, flash memory, EEPROM, battery-backed RAM such as S-RAM or D-RAM and any other type of digital data storage component. In some embodiments, the electronic circuit or electronic component includes volatile memory. In some embodiments, the electronic circuit or electronic component includes non-volatile memory. In some embodiments, the electronic circuit or electronic component can include transistors interconnected to provide positive feedback operating as latches or flip flops, providing for circuits that have two or more metastable states, and remain in one of these states until changed by an external input. Data storage can be based on such flip-flop containing circuits. Data storage can also be based on the storage of charge in a capacitor or on other principles. In some embodiments, the non-volatile memory 808 can be integrated with the control circuit 890.

In various embodiments the condition sensing system 310 can include a clock circuit 810 disposed within the housing 314. In some embodiments, the clock circuit 810 can be integrated with the control circuit 890. While not shown in FIG. 8, it will be appreciated that various embodiments herein can include a data/communication bus to provide for the transportation of data between components. In some embodiments, an analog signal interface can be included. In some embodiments, a digital signal interface can be included.

In various embodiments the condition sensing system 310 can include a communications circuit 812. In various embodiments, the communications circuit can include components such as an antenna 814, amplifiers, filters, digital to analog and/or analog to digital converters, and the like.

In various embodiments the fluid condition sensing system 310 can also include a geolocation chip or circuit 822. Geolocation data can include latitude/longitude coordinates, or other location identifying information such as a nearest address, nearest landmark, etc. As used herein, the term "geolocation data" shall include reference to all location identifying data, unless the context dictates otherwise.

In some cases, geolocation data can be derived from a satellite-based geolocation system. Such systems can include, but are not limited to, GPS L1/L2, GLONASS G1/G2, BeiDou B1/B2, Galileo E1/E5b, SBAS, or the like. In various embodiments, the geolocation circuit 822 can include appropriate signal receivers or transceivers to interface with a satellite and/or the geolocation circuit can interface with and/or receive data from a separate device or system that provides geolocation data or derives geolocation data from a satellite or other device. However, it will be appreciated that geolocation data herein is not limited to just that which can be received from or derived from interface with a satellite. Geolocation data can also be derived from addresses, beacons, landmarks, various referential techniques, IP address evaluation, and the like.

Figure 9:
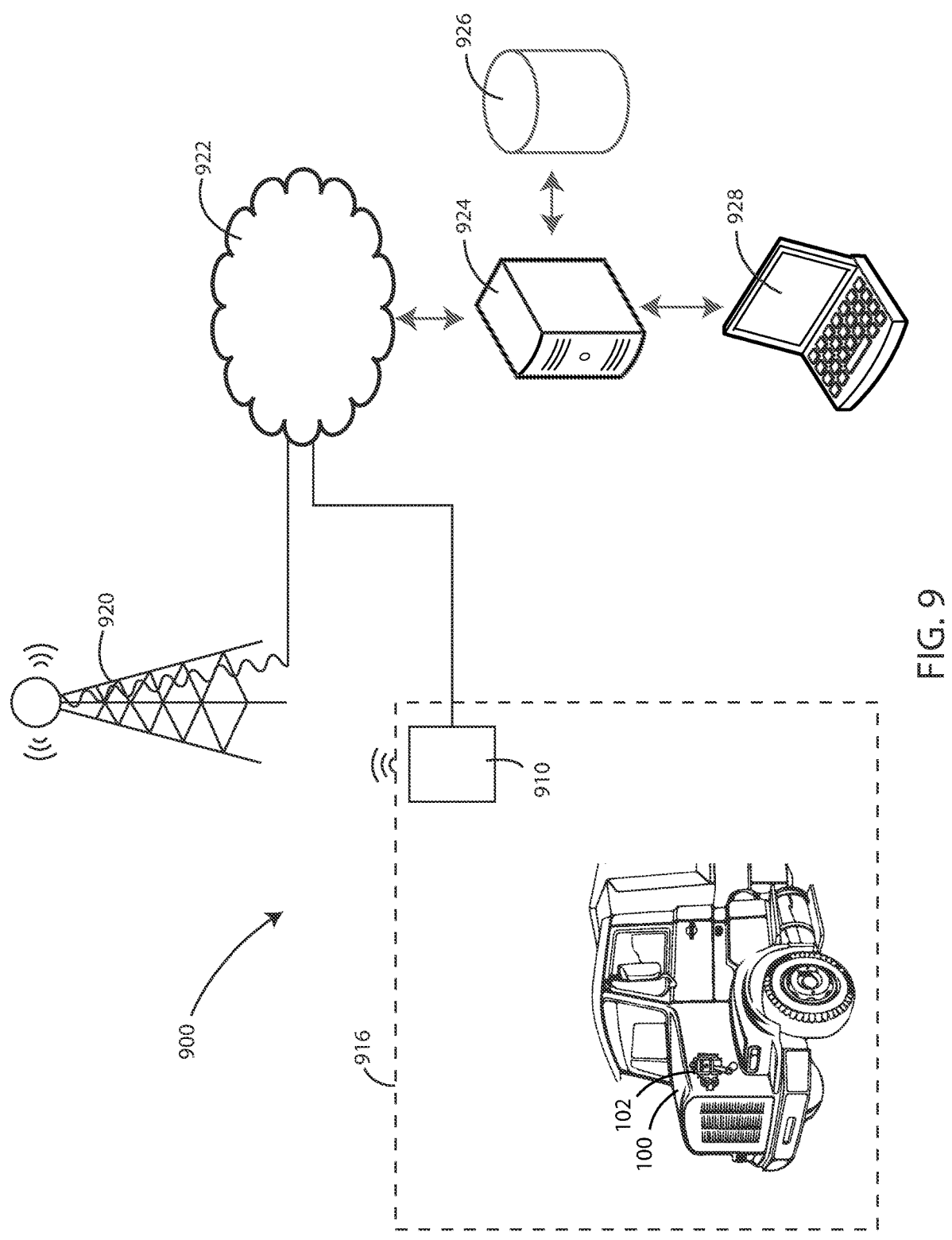
FIG. 9 is a schematic view of a data exchange network in accordance with various embodiments herein.

Referring now to FIG. 9, a schematic view of a data exchange network 900 is shown in accordance with various embodiments herein. FIG. 9 shows a vehicle 100. The vehicle 100 includes an engine 102 and can have a lubrication system and a condition sensing system (not shown in this view) therein. In this view, the vehicle is within a local environment 916. In some embodiments, the local environment can include a communication repeater 910 or router (which can be on-vehicle or off-vehicle) that can provide communications with the cloud 922. However, in some embodiments, the condition sensing system or another system in communication therewith can communicate directly with a cell tower 920, which can in turn provide communications with the cloud 922.

The data exchange network 900 can also include a remote server 924 or cloud server, which can be real or virtual. The data exchange network 900 can also include a remote database 926 or cloud database, which can also be real or virtual. In some embodiments, a remote user interface 928 can be included, which can be used by a fleet manager or another individual. In some cases, alerts or other communications referred to herein can be delivered through the cloud 922 or another communication network and to a remote user interface 928.

Figure 10:
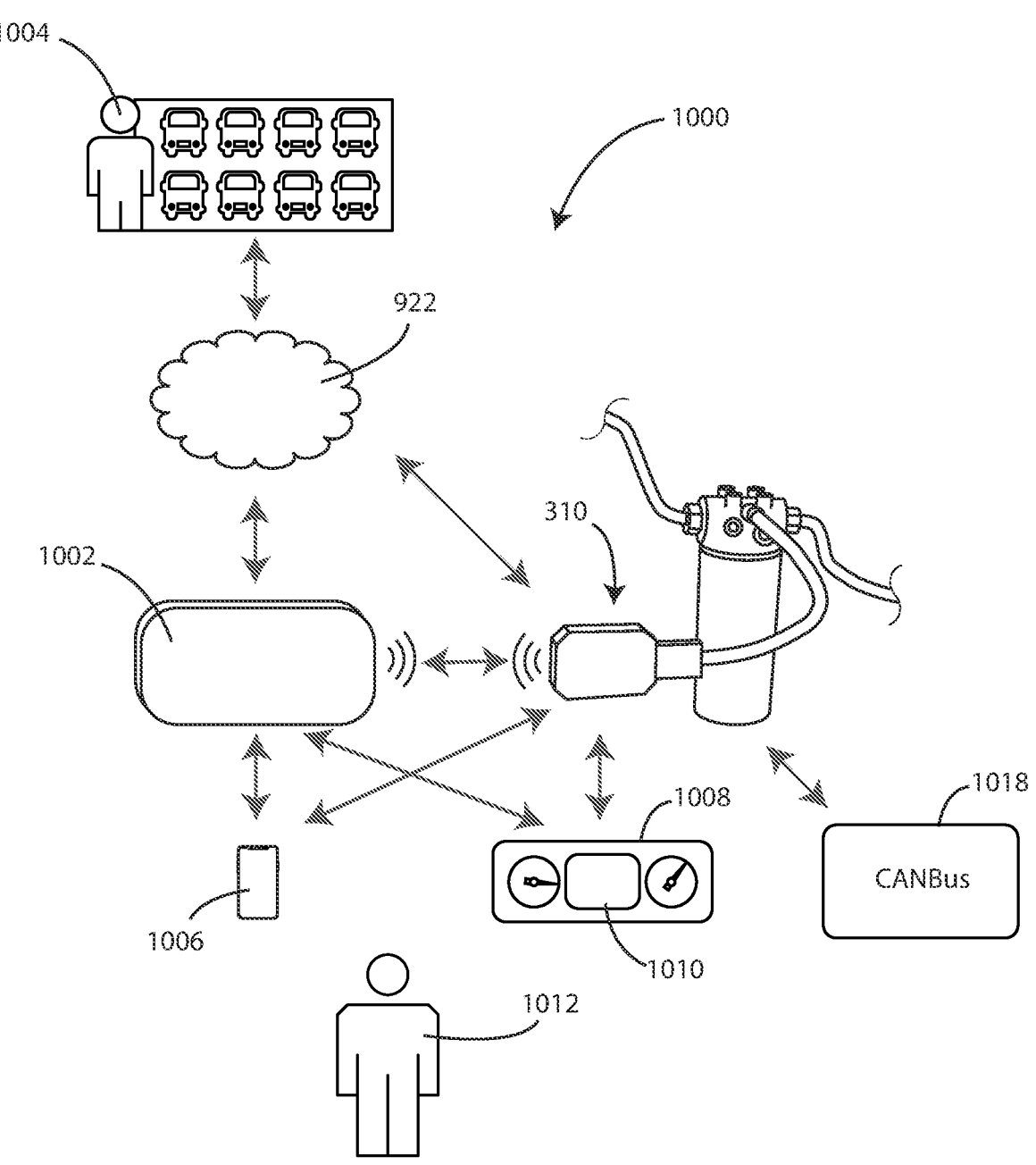
FIG. 10 is a schematic view of a data exchange network in accordance with various embodiments herein.

Many different options are contemplated for the exchange of data herein. Referring now to FIG. 10, a schematic view of a data exchange network 1000 is shown in accordance with various embodiments herein. FIG. 10 shows a fluid condition sensing system 310. The fluid condition sensing system 310 can be in communication with a data communicator 1002. In this scenario, the data communicator 1002 can serve as a link for conveying data to an external network as well as to other system (on-vehicle or off-vehicle).

In this example, the data exchange network 1000 can also include a personal data device 1006. The personal data device 1006 can be, for example, a smart phone, a tablet computing device, or other computing device. The personal data device 1006 can exchange data with the data communicator 1002 and/or the fluid condition sensing system 310. The personal data device 1006 can be used to convey alerts or other information to a vehicle operator 1012.

In this example, the data exchange network 1000 is also shown to include a vehicle data display 1008. The vehicle data display 1008 can include a video display 1010 for conveying information to the vehicle operator 1012.

In some embodiments, the system can receive data from and/or send data to a vehicle data network, such as a CANBus network 1018. "CANBus" refers to a vehicle data bus standard designed to allow devices and electronic control units to communicate with one another. Many vehicles include a CANBus network and communication with the CANBus network can provide many different types of data. For example, interfacing with the CANBus network can provide one or more of fuel level data, engine RPM data, engine hours of operation data, odometer data, engine/vehicle temperature data, fuel consumption data, fuel system data, ambient temperature data, geolocation data, fuel flow-rate and the like.

In various embodiments, the system can use data received from a CANBus network to determine whether or not the engine has been turned off and/or started up after being turned off. This information can be utilized by the system herein in evaluating whether or not an oil change event has occurred. An engine being turned off and/or started up can also be determined in other ways. In some embodiments, the system can include an accelerometer or other vibration sensor and detect the existence or absence of characteristic vibrations associated with the engine running to determine whether or not the engine has been shut off or started up and currently running.

Thus, in some embodiments, the system can evaluate information regarding whether the vehicle's engine has been started up after being shut off in determining whether or not an oil change event has occurred. For example, while it is possible that a step change in fluid property values can occur during continuous vehicle operation (such as from a component failing and resulting in sudden coolant contamination—as one example) a step change in fluid property values occurring during continuous vehicle operation generally does not indicate that an oil change event has occurred. As such, in some embodiments, the system can evaluate whether or not changes in fluid property values coincide and follow shortly after an engine startup event. In some embodiments, if no engine startup event has occurred within a window of preceding time, then the system does not characterize the observed change in fluid properties as an oil change event and, therefore, does not execute other actions such as setting the newly observed fluid properties as new baseline value(s). The window of preceding time can vary. In some embodiments, the window of preceding time can be sufficiently long to provide for warmup of the engine. In some embodiments, the window of preceding time can be greater than or equal to 0.5, 3, 5, 7, or 10 minutes. In some embodiments, the window of preceding time is less than or equal to 30, 15, 12, or 10 minutes. In some embodiments, the window of preceding time can fall within a range between any of the preceding values.

In some embodiments, the fluid condition sensing system 310 can be used to directly exchange data with the CANBus network 1018. However, in other embodiments, data may be exchanged indirectly such as by passing through the data communicator 1002 or another component as an intermediary.

In various embodiments, the data communicator 1002 and/or the fluid condition sensing system 310 can send data to and receive data from the cloud 922 or another data network. A fleet manager 1004 can, in turn, receive data from and/or send data to the cloud 922 or another data network.

In various embodiments herein, the system can issue alerts and/or provide other information to other systems and/or to individuals such as the fleet manager 1004 and/or the vehicle operator 1012. By way of example, in various embodiments, the fluid condition sensing system 310 can be configured to issue an alert when a fluid property, such as a current viscosity value, differs from a recorded fluid property value by an amount crossing a threshold value. As described elsewhere herein, the threshold value can be a percentage value or a predetermined or dynamically determined absolute value.

In various embodiments, the fluid condition sensing system 310 can be configured to estimate a time when an oil change is needed based on a rate of change of measured viscosity values versus the baseline viscosity value. This can be done in various ways. In some embodiments, the system can calculate an equation for a curve that fits the observed rate of change of measured property values and then use this equation to derive the expected time when such property values will hit a point indicating that an oil change is needed. The equation for a curve can be determined using standard mathematical curve fitting techniques resulting in a first degree, second degree, third degree polynomial, or n degree polynomial equation and evaluated using a least squares or other technique. The fluid condition sensing system 310 can also be configured to send an alert or other communication including information including the estimated time when an oil change is needed.

In various embodiments, the fluid condition sensing system 310 can be configured to send an alert when new baseline fluid property data after an oil change event has occurred that differs from a predetermined expected value by a threshold amount. In various embodiments, the fluid condition sensing system 310 can be configured to identify a type of oil present after a detected oil change event based on at least one type of data from the fluid property sensor selected from viscosity and dielectric properties and send an alert indicating the type of oil present. In various embodiments, the fluid condition sensing system 310 can be configured to identify a type of oil present after a detected oil change event based on at least one type of data from the fluid property sensor and send an alert to the fleet manager 1004 if the type of oil is out of specification.

In some embodiments, other types of data can be utilized to more accurately determine when an oil change event has taken place. For example, in some embodiments, geolocation data can be used to cross-reference a vehicle's location when a change in fluid properties is observed against service locations where an oil change or other service event would be likely to have taken place. The system can change threshold values (such as lowering threshold values) for criteria used to indicate that an oil change event has occurred if the observed change has occurred at a service location as determined by evaluating geolocation data. Conversely, the system can change threshold values (such as by increasing threshold values) for criteria used to indicate that an oil change event has occurred if the observed change has occurred at a location that is not a service location as determined by evaluating geolocation data. In this way, determinations of whether oil change events have occurred can be made more accurate.

Figure 11:
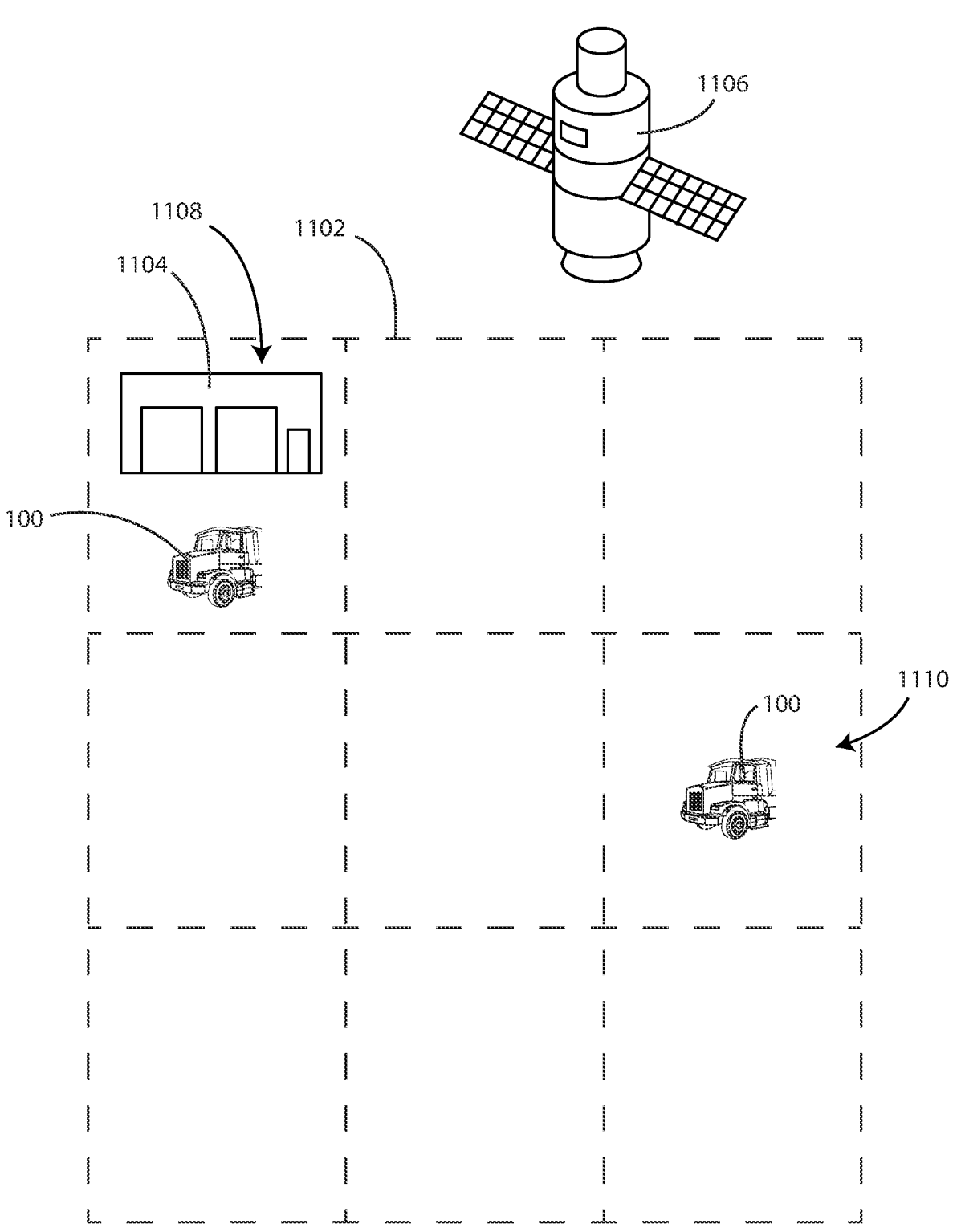
FIG. 11 is a schematic view of a geolocation system in accordance with various embodiments herein.

Referring now to FIG. 11, a schematic view of a geolocation system is shown in accordance with various embodiments herein. FIG. 11 shows a vehicle 100 and a geolocation grid 1102. FIG. 11 also shows a geolocation satellite 1106. In this view, both a vehicle 100 and a service facility 1104 are located at a first location 1108 in the geolocation grid 1102. If a change in fluid properties was observed while the vehicle 100 was in the first location 1108 (along with the service facility 1104) then the system can be configured to be more likely to determine that an oil change event has occurred (e.g., the detection of an oil change event can be made more sensitive such as by reducing threshold values required to declare that an oil change event has occurred). FIG. 11 also shows a vehicle 100 at a second location 1110. The second location 1110 does not include a service facility 1104. If a change in fluid properties was observed while the vehicle is in the second location 1110, then the system can be configured to be less likely to determine that an oil change event has occurred (e.g., the detection of an oil change event can be made less sensitive such as by increasing threshold values required to declare that an oil change event has occurred). As such, in various embodiments herein, the fluid condition sensing system 310 can be configured to evaluate geolocation data when automatically detecting when the oil change event 506 has occurred.

In some embodiments, geolocation data can be recorded and provided along with alerts and/or other data transmissions herein. For example, in some embodiments, alerts or other communications sent to a fleet manager can also include geolocation information. In some embodiments, when the system detects an oil change event, the geolocation data can be recorded and stored in a database (local to the vehicle or located remotely in the cloud). In some embodiments, detection of certain contamination states or scenarios (such as an out of specification oil detected) the system can record geolocation data associated with event and/or include such geolocation data along with any alerts or communications that are generated regarding the same.

Pattern/Template Generation and Pattern Matching for Identification of Fluid Change Events It will be appreciated that in various embodiments herein, the system can be used to detect a pattern or patterns of data indicative of an oil change event. Such patterns can be detected in various ways. Some techniques are described elsewhere herein, but some further examples will now be described.

In some embodiments, fluid change events can be identified based on identifying or matching characteristic patterns in the data from a fluid property sensor and/or other sensors. For example, a "positive" pattern for sensor data associated with an oil change event can be stored by the system and current data can be periodically matched against such a pattern. If a match exceeding a threshold value is found, then a fluid change event can be deemed to have taken place. As another example, a "negative" pattern for sensor data associated with a fluid change event can be stored by the system and current data can be periodically matched against such a pattern.

In some embodiments, one or more sensors (such as a fluid property sensor) can be operatively connected to a controller (such as the control circuit 890 described in FIG. 8) or another processing resource (such as a processor of another device or a processing resource in the cloud). The control circuit 890 or other processing resource can be adapted to receive data representative of an oil change event from one or more of the sensors and/or determine statistics of the system over a monitoring time period based upon the data received from the sensor(s). As used herein, the term "data" can include a single datum or a plurality of data values or statistics. The term "statistics" can include any appropriate mathematical calculation or metric relative to data interpretation, e.g., probability, confidence interval, distribution, range, or the like. Further, as used herein, the term "monitoring time period" means a period of time over which characteristics of the filtration system are measured and statistics are determined. The monitoring time period can be any suitable length of time, e.g., 1 second, 10 seconds, 30 seconds, 1 minute, 10 minutes, 30 minutes, 1 hour, 1 day, 1 week, 1 month, etc., or a range of time between any of the foregoing time periods.

Any suitable technique or techniques can be utilized to determine statistics for the various data from the sensor(s), e.g., direct statistical analyses of time series data from the sensors, differential statistics, comparisons to baseline or statistical models of similar data, etc. Such techniques can be general or system-specific and represent long-term or short-term operational behavior. These techniques could include standard pattern classification methods such as Gaussian mixture models, clustering as well as Bayesian approaches, machine learning approaches such as neural network models and deep learning, and the like.

Further, in some embodiments, the control circuit 890, or another component of the system, can be adapted to compare data, data features, and/or statistics against various other patterns, which could be predetermined or starting patterns (baseline patterns) based on the type or model of the engine, vehicle, lubrication system, oil or oil filter, etc., one or more predetermined patterns that serve as patterns indicative of an occurrence of an oil change event (positive example patterns), one or more predetermined patterns that serve as patterns indicative of the absence of an oil change event (negative example patterns), or the like. As merely one scenario, if a pattern is detected by the system that exhibits similarity crossing a threshold value to a particular positive example pattern or substantial similarity to that pattern, wherein the pattern is specific for an oil change event, then that can be taken as an indication by the system that an oil change event has occurred.

Similarity and dissimilarity can be measured directly via standard statistical metrics such normalized Z-score, or similar multidimensional distance measures (e.g., Mahalanobis or Bhattacharyya distance metrics), or through similarities of modeled data and machine learning. These techniques can include standard pattern classification methods such as Gaussian mixture models, clustering as well as Bayesian approaches, neural network models, and deep learning.

As used herein the term "substantially similar" means that, upon comparison, the sensor data are congruent or have statistics fitting the same statistical model, each with an acceptable degree of confidence. The threshold for the acceptability of a confidence statistic may vary depending upon the vehicle, engine, lubrication system, oil condition sensing system, sensor(s), sensor arrangement, type of data, context, condition, etc.

The statistics associated with the operational status of a filtration system over the monitoring time period, can be determined by utilizing any suitable technique or techniques, e.g., standard pattern classification methods such as Gaussian mixture models, clustering, hidden Markov models, as well as Bayesian approaches, neural network models, and deep learning.

Various embodiments herein specifically include the application of a machine learning classification model. In various embodiments, the oil condition sensing system can be configured to periodically update the machine learning classification model based on indicators of oil change events. In some embodiments, user input can be used to positively identify an oil change event and then this information can be used as part of a supervised machine learning approach to positively characterize patterns associated with oil change events.

In some embodiments, a training set of data can be used to generate a machine learning classification model. The input data can include sensor data as described herein as tagged/labeled with binary and/or non-binary classifications of oil change events. Binary classification approaches can utilize techniques including, but not limited to, logistic regression, k-nearest neighbors, decision trees, support vector machine approaches, naive Bayes techniques, and the like. Multi-class classification approaches (e.g., for non-binary classifications of stress) can include k-nearest neighbors, decision trees, naive Bayes approaches, random forest approaches, and gradient boosting approaches amongst others.

Methods

Many different methods are contemplated herein, including, but not limited to, methods of making, methods of using, and the like. Aspects of system/device operation described elsewhere herein can be performed as operations of one or more methods in accordance with various embodiments herein.

Figure 12:
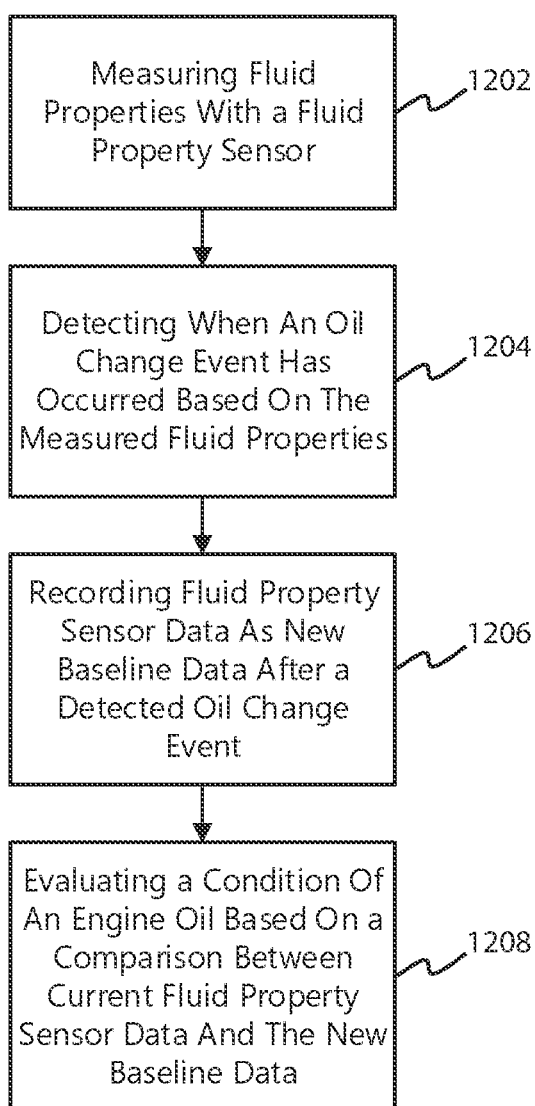
FIG. 12 is a schematic view of operations of a method in accordance with various embodiments herein.

Referring now to FIG. 12, a schematic view of operations of an exemplary method is shown in accordance with various embodiments herein. The method of monitoring fluid conditions can include an operation of measuring fluid properties with a fluid property sensor 1202. The method of monitoring fluid conditions also includes an operation of detecting when a fluid change event has occurred based on the measured fluid properties 1204. The method of monitoring fluid conditions can also include an operation of recording fluid property sensor data as new baseline data after a detected fluid change event 1206. The method of monitoring fluid conditions can also include an operation of evaluating a condition of an engine fluid based on a comparison between current fluid property sensor data and the new baseline data 1208.

In an embodiment, the method can further include evaluating whether current fluid property sensor data including one or more of viscosity, density, temperature, dielectric constant, and resistivity fall within a predetermined range before the operation of the evaluating a condition of an engine fluid based on a comparison between current fluid property sensor data and the new baseline data.

In an embodiment, the method can further include evaluating whether a current temperature differs from a temperature when new baseline data was recorded by more than a threshold value before the operation of the evaluating a condition of an engine fluid based on a comparison between current fluid property sensor data and the new baseline data.

In an embodiment of the method, detecting when the fluid change event has occurred further comprises evaluating signals from the fluid property sensor and interpreting a change in viscosity crossing a threshold value as a fluid change event. In an embodiment of the method, viscosity data is utilized as a moving average. In an embodiment, the method can further include normalizing viscosity data based on temperature data.

In an embodiment of the method, detecting when the fluid change event has occurred further comprises evaluating signals from the fluid property sensor and interpreting a change in dielectric constant crossing a threshold value as a fluid change event.

In an embodiment, the method can further include evaluating data from a drain plug sensor. In an embodiment, the method can further include automatically detecting the fluid change event by evaluating signals from the fluid property sensor and the drain plug sensor and interpreting a change in viscosity crossing a threshold value that is correlated with or otherwise coincides with a drain plug removal event as a fluid change event.

In an embodiment, the method can further include utilizing viscosity sensor data only when a measured temperature falls within a predetermined temperature range. In an embodiment, the predetermined temperature range can include from 90 to 125 degrees Celsius. However, it will be appreciated that as described elsewhere herein that the optimal temperature range can vary depending on the type of contamination that is being detected/measured.

In an embodiment, the method can further include issuing an alert when a current viscosity value differs from a recorded viscosity value by an amount crossing a threshold value. In an embodiment, the method can further include estimating a time when a fluid change is needed based on a rate of change of measured viscosity values versus the baseline viscosity value. In an embodiment, the method can further include issuing an alert when a current dielectric constant value differs from a recorded dielectric constant value by an amount crossing a threshold value. In an embodiment, the method can further include estimating a time when a fluid change is needed based on a rate of change of measured dielectric constant values versus the baseline dielectric constant value. In an embodiment, the method can further include sending an alert when new baseline fluid property data after a fluid change event has occurred differs from a predetermined expected value by a threshold amount.

In an embodiment, the method can further include identifying a type of fluid present after a detected fluid change event based on at least one type of data from the fluid property sensor selected from viscosity and dielectric properties and send an alert indicating the type of fluid present. In an embodiment, the method can further include sending an alert to a fleet manager if the type of fluid is out of specification.

In an embodiment of the method, the fluid property sensor measures at least two of viscosity, density, temperature, impedance, dielectric constant, and resistivity of engine oil. In an embodiment of the method, the fluid property sensor measures at least three of viscosity, density, temperature, impedance, dielectric constant, and resistivity of engine oil. In an embodiment of the method, the fluid property sensor measures at least four of viscosity, density, temperature, impedance, dielectric constant, and resistivity of engine oil. In an embodiment of the method, the fluid property sensor measures at least five of viscosity, density, temperature, impedance, dielectric constant, and resistivity of engine oil. In an embodiment of the method, the fluid property sensor measures all of viscosity, density, temperature, impedance, dielectric constant, and resistivity of engine oil.

In an embodiment, the method can further include determining an engine oil contamination state based on data from the fluid property sensor. In an embodiment, the method can further include classifying the engine oil contamination state as having a slow evolution speed or a high evolution speed. In an embodiment, the method can further include classifying the value of each engine oil contamination state parameter into one of three categories. As one example, the three categories can include a normal category, an elevated category, and a high category that represents a need for urgent action. Information regarding the category can be conveyed to a vehicle operator, a fleet manager, or another individual.

In an embodiment, the method can further include classifying the engine oil contamination state using current data reflecting one or more of viscosity, density, dielectric constant, and resistivity in comparison with baseline data for the same. In an embodiment, the method can further include classifying the engine oil contamination state as being coolant or water contamination if dielectric constant increases, viscosity is stable, and resistivity decreases. In an embodiment, the method can further include classifying the engine oil contamination state as being fuel dilution if viscosity decreases and other parameters are stable. In an embodiment, the method can further include classifying the engine oil contamination state as being soot contamination if viscosity increases and dielectric constant increases. In an embodiment, the method can further include classifying the engine oil contamination state as being oxidation if viscosity increases, dielectric constant is stable, and resistivity decreases.

In an embodiment, methods herein can include classifying the engine oil age (with respect to a useful service life of the engine oil) based on increases in dielectric constant (as may be normalized based on temperature and/or other parameters).

In an embodiment, the method can further include evaluating geolocation data when automatically detecting when the oil change event has occurred.

In an embodiment, the method can further include recording fluid property sensor data as new baseline data after a detected oil change event across a range of temperatures.

It will be appreciated that although oil condition sensing systems herein have been demonstrated with respect to an on-vehicle implementation, it is also contemplated that similar systems can be used in off-vehicle implementations and/or in the context of engines that are a part of stationary equipment instead of vehicles. For example, engines associated with stationary generators also utilize oil-based lubrication systems. As such, in some embodiments, systems herein can be used in conjunction with any equipment containing an engine and an oil-based lubrication system whether a vehicle, another type of equipment, a mobile piece of equipment, a stationary piece of equipment, or the like.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A fluid condition sensing system comprising:
a control circuit;
a temperature sensor, wherein the temperature sensor is in signal communication with the control circuit; and
a fluid property sensor, wherein the fluid property sensor interfaces with engine oil in an engine lubrication system of a vehicle;
wherein the fluid property sensor is in signal communication with the control circuit;
wherein the fluid property sensor measures fluid properties including at least a dielectric constant;
wherein the fluid condition sensing system is configured to:
measure the dielectric constant of the engine oil with the fluid property sensor over time;
automatically detect when a fluid change event has occurred based on detecting a step change in the dielectric constant of the engine oil and exceeding a threshold value in less than a fixed period of vehicle operation time with the fluid property sensor;
upon detecting the fluid change event, measure fluid properties of the engine oil with the fluid property sensor and record the measured fluid properties as new baseline fluid property data after the fluid change event has occurred; and
evaluate the condition of the engine oil with the fluid property sensor based on a comparison with the new baseline fluid property data; and
generate an alert to a vehicle operator or system based on the fluid property sensor detecting a current fluid property of the engine oil that differs from the new baseline fluid property data by an amount exceeding a contamination threshold.

2. The fluid condition sensing system of claim 1, wherein the fluid property sensor also measures viscosity of fluid.

3. The fluid condition sensing system of claim 1, further comprising a drain plug sensor, wherein the drain plug sensor is in signal communication with the control circuit.

4. The fluid condition sensing system of claim 3, wherein the fluid condition sensing system is configured to automatically detect the fluid change event by evaluating signals from the fluid property sensor and the drain plug sensor and interpret a change in dielectric constant crossing a threshold value that is correlated with a drain plug removal event as the fluid change event.

5. The fluid condition sensing system of claim 1, wherein the fluid condition sensing system is configured to estimate a time when a fluid change is needed based on a rate of change of measured dielectric constant values versus the baseline dielectric constant value.

6. The fluid condition sensing system of claim 1, wherein the fluid condition sensing system is configured to identify a type of fluid present after the fluid change event based on at least one type of data from the fluid property sensor selected from viscosity and dielectric constant value and send an alert indicating the type of fluid present.

7. The fluid condition sensing system of claim 1, wherein the fluid condition sensing system is configured to identify a type of fluid present after the fluid change event based on at least one type of data from the fluid property sensor and send an alert to a fleet manager if the type of fluid is out of specification.

8. The fluid condition sensing system of claim 1, wherein the fluid condition sensing system is configured to determine a fluid contamination state based on data from the fluid property sensor.

9. The fluid condition sensing system of claim 8, wherein the fluid contamination state includes the presence and/or amount of at least one of ingressed contaminants and generated contaminants.

10. The fluid condition sensing system of claim 8, wherein the fluid contamination state includes at least one of oxidation state, water contamination, coolant contamination, fuel contamination, soot contamination, metal contamination, total base number value, total acid number value, and incorrect fluid presence.

11. The fluid condition sensing system of claim 8, wherein the fluid condition sensing system is configured to determine fluid water contamination and coolant contamination when a measured temperature of the fluid is less than a boiling temperature of water at a location of the fluid being evaluated by the fluid condition sensing system.

12. The fluid condition sensing system of claim 8, wherein the fluid condition sensing system is configured to classify the fluid contamination state using current data reflecting viscosity, density, dielectric constant, and resistivity in comparison with baseline data for the same.

13. The fluid condition sensing system of claim 1, wherein the fluid condition sensing system is configured to:

store at least one positive pattern for sensor data associated with an oil change event;

store at least one negative pattern for sensor data not associated with the oil change event;

compare current data from the fluid property sensor against the at least one positive pattern and the at least one negative pattern to determine whether the oil change event has occurred.

14. The fluid condition sensing system of claim 2, wherein the fluid condition sensing system is configured to utilize the viscosity measured by the fluid property sensor only when a measured temperature of the fluid falls within a predetermined temperature range.

15. The fluid condition sensing system of claim 1, wherein the step change is detected when the measured dielectric constant of the engine oil changes by at least 10 percent in less than a fixed period of time.

16. The fluid condition sensing system of claim 1, wherein the fixed period of time is five minutes.

17. The fluid condition sensing system of claim 1, further comprising a geolocation circuit; wherein the fluid condition sensing system is configured to:

determine a location of the vehicle when a change in fluid properties is detected with the geolocation circuit;

lower the threshold value for determining the fluid change event when the location of the vehicle is at or near a service location;

raise the threshold value for determining the fluid change event when the location of the vehicle is not at or near the service location.

18. A fluid condition sensing system comprising:

a control circuit;

a temperature sensor, wherein the temperature sensor is in signal communication with the control circuit; and a fluid property sensor, wherein the fluid property sensor interfaces with engine oil in an engine lubrication system of a vehicle;

wherein the fluid property sensor is in signal communication with the control circuit;

34 wherein the fluid property sensor measures fluid properties including at least a fluid acid number of the engine oil;

wherein the fluid condition sensing system is configured to:

measure the fluid acid number of the engine oil with the fluid property sensor over time;

automatically detect when a fluid change event has occurred based on detecting a decrease in the fluid acid number of the engine oil and exceeding a threshold value in less than a fixed period of vehicle operation time with the fluid property sensor;

upon detecting the fluid change event, measure fluid properties of the engine oil with the fluid property sensor and record the measured fluid properties as new baseline fluid property data after the fluid change event has occurred; and evaluate the condition of the engine oil based on a comparison with the new baseline fluid property data; and generate an alert to a vehicle operator or system based on the fluid property sensor detecting a current fluid property of the engine oil that differs from the new baseline fluid property data by an amount exceeding a contamination threshold.

19. A method of monitoring fluid conditions comprising:

measuring fluid properties with a fluid property sensor, wherein the fluid property sensor interfaces with engine oil in an engine lubrication system of a vehicle, wherein measuring fluid properties comprises measuring a dielectric constant of the engine oil with the fluid property sensor over time;

detecting when a fluid change event has occurred based on the measured fluid properties based on detecting a step change in the dielectric constant of the engine oil and exceeding a threshold value in less than fixed period of vehicle operation time with the fluid property sensor;

upon detecting the fluid change event, measuring fluid properties of the engine oil with the fluid property sensor and recording the measured fluid properties as new baseline data after a detected oil change event; and evaluating a condition of the engine oil based on a comparison between current fluid property sensor data and the new baseline data; and generating an alert to a vehicle operator or system based on the fluid property sensor detecting a current fluid property of the engine oil that differs from the new baseline fluid property data by an amount exceeding a contamination threshold.

20. A hydraulic fluid condition sensing system comprising:

a control circuit;

a temperature sensor, wherein the temperature sensor is in signal communication with the control circuit; and a fluid property sensor;

wherein the fluid property sensor is in signal communication with the control circuit;

wherein the fluid property sensor interfaces with engine oil in an engine lubrication system of a vehicle;

wherein the fluid property sensor measures fluid properties including at least an acid number of the engine oil;

wherein the hydraulic fluid condition sensing system is configured to:

measure the acid number of the engine oil with the fluid property sensor over time;

automatically detect when a fluid change event has occurred based on detecting a decrease in the acid number of the engine oil and exceeding a threshold value in less than a fixed period of vehicle operation time with the fluid property sensor;

upon detecting the fluid change event, measure fluid properties of the engine oil with the fluid property sensor and record the measured fluid properties as new baseline fluid property data after the fluid change event has occurred; and evaluate the condition of the engine oil based on a comparison with the new baseline fluid property data; and generate an alert to a vehicle operator or system based on the fluid property sensor detecting a current fluid property of the engine oil that differs from the new baseline fluid property data by an amount exceeding a contamination threshold.

* * * * *